United States Patent
Waydo et al.

(10) Patent No.: US 10,524,735 B2
(45) Date of Patent: Jan. 7, 2020

(54) DETECTING CONDITIONS USING HEART RATE SENSORS

(71) Applicant: APPLE INC., Cupertino, CA (US)

(72) Inventors: Stephen J. Waydo, Campbell, CA (US); Christopher J. Brouse, Cupertino, CA (US); Ian R. Shapiro, Saratoga, CA (US); Joseph C. McBride, San Jose, CA (US); Michael O'Reilly, San Jose, CA (US); Myra Mary Haggerty, San Mateo, CA (US)

(73) Assignee: Apple Inc., Cupertino, CA (US)

( * ) Notice: Subject to any disclaimer, the term of this patent is extended or adjusted under 35 U.S.C. 154(b) by 37 days.

(21) Appl. No.: 15/889,046

(22) Filed: Feb. 5, 2018

(65) Prior Publication Data

US 2018/0279956 A1 Oct. 4, 2018

Related U.S. Application Data

(60) Provisional application No. 62/557,013, filed on Sep. 11, 2017, provisional application No. 62/541,269, (Continued)

(51) Int. Cl.
*A61B 5/00* (2006.01)
*G16H 50/20* (2018.01)
(Continued)

(52) U.S. Cl.
CPC .......... *A61B 5/721* (2013.01); *A61B 5/02416* (2013.01); *A61B 5/02433* (2013.01);
(Continued)

(58) Field of Classification Search
None
See application file for complete search history.

(56) References Cited

U.S. PATENT DOCUMENTS

| 5,483,261 A | 1/1996 | Yasutake |
| 5,488,204 A | 1/1996 | Mead et al. |

(Continued)

FOREIGN PATENT DOCUMENTS

| CN | 106031632 A | 10/2016 |
| JP | 2000-163031 A | 6/2000 |

(Continued)

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Michael R Bloch
(74) *Attorney, Agent, or Firm* — Brownstein Hyatt Farber Schreck, LLP

(57) ABSTRACT

This relates to methods for measuring irregularities in a signal and corresponding devices. The devices can include a PPG sensor unit configured to detect multiple occurrences of a given event in the measured signal(s) over a sampling interval. In some instances, the device can register the occurrences of the events. In some examples, the device can include one or more motion sensors configured to detect whether the device is in a low-motion state. The device may delay initiating measurements when the device is not in a low-motion state to enhance measurement accuracy. Examples of the disclosure further include resetting the sample procedure based on one or more factors such as the number of non-qualifying measurements. In some examples, the device can be configured to perform both primary and secondary measurements, where the primary measurements can include readings using a set of operating conditions different from the secondary measurements.

6 Claims, 15 Drawing Sheets

Related U.S. Application Data filed on Aug. 4, 2017, provisional application No. 62/480,127, filed on Mar. 31, 2017, provisional application No. 62/478,030, filed on Mar. 28, 2017.

(51) Int. Cl.
| | |
|---|---|
| *A61B 5/024* | (2006.01) |
| *A61B 5/0245* | (2006.01) |
| *A61B 5/11* | (2006.01) |
| *G16H 40/63* | (2018.01) |

(52) U.S. Cl.
CPC ...... *A61B 5/02438* (2013.01); *A61B 5/02455* (2013.01); *A61B 5/1118* (2013.01); *A61B 5/681* (2013.01); *A61B 5/7221* (2013.01); *A61B 5/7282* (2013.01); *A61B 5/742* (2013.01); *A61B 5/746* (2013.01); *G16H 40/63* (2018.01); *G16H 50/20* (2018.01); *A61B 5/02405* (2013.01); *A61B 5/6898* (2013.01); *A61B 2505/07* (2013.01); *A61B 2560/0209* (2013.01); *A61B 2562/0219* (2013.01)

(56) References Cited

U.S. PATENT DOCUMENTS

| | | | |
|---|---|---|---|
| 5,825,352 A | 10/1998 | Bisset et al. | |
| 5,835,079 A | 11/1998 | Shieh | |
| 5,880,411 A | 3/1999 | Gillespie et al. | |
| 6,188,391 B1 | 2/2001 | Seely et al. | |
| 6,310,610 B1 | 10/2001 | Beaton et al. | |
| 6,323,846 B1 | 11/2001 | Westerman et al. | |
| 6,690,387 B2 | 2/2004 | Zimmerman et al. | |
| 7,015,894 B2 | 3/2006 | Morohoshi | |
| 7,184,064 B2 | 2/2007 | Zimmerman et al. | |
| 7,252,639 B2 * | 8/2007 | Kimura | A61B 5/02416 600/322 |
| 7,471,969 B2 * | 12/2008 | Diab | A61B 5/14551 600/323 |
| 7,663,607 B2 | 2/2010 | Hotelling et al. | |
| 8,479,122 B2 | 7/2013 | Hotelling et al. | |
| 9,314,174 B1 | 4/2016 | Brady et al. | |
| 9,357,936 B2 * | 6/2016 | Rodriguez-Llorente | A61B 5/02416 |
| 2002/0137995 A1 * | 9/2002 | Heckel | A61B 5/14551 600/323 |
| 2005/0075553 A1 | 4/2005 | Sakai et al. | |
| 2005/0234358 A1 | 10/2005 | Cao et al. | |
| 2006/0197753 A1 | 9/2006 | Hotelling | |
| 2006/0211925 A1 * | 9/2006 | Lamego | A61B 5/14552 600/310 |
| 2011/0237912 A1 * | 9/2011 | Couronne | A61B 5/14551 600/323 |
| 2013/0137946 A1 | 5/2013 | Geske et al. | |
| 2013/0324809 A1 | 12/2013 | Lisogurski et al. | |
| 2014/0018686 A1 | 1/2014 | Medelius et al. | |
| 2014/0171769 A1 | 6/2014 | Ochs et al. | |
| 2014/0180042 A1 * | 6/2014 | Addison | A61B 5/14551 600/324 |
| 2014/0243633 A1 * | 8/2014 | Addison | A61B 5/14552 600/340 |
| 2014/0276154 A1 | 9/2014 | Katra et al. | |
| 2015/0208962 A1 * | 7/2015 | Baker, Jr. | A61B 5/1495 600/331 |
| 2015/0245782 A1 * | 9/2015 | Morland | A61B 5/0095 600/301 |
| 2015/0250385 A1 | 9/2015 | Ahmed et al. | |
| 2016/0026212 A1 | 1/2016 | Lee et al. | |
| 2016/0066844 A1 | 3/2016 | Venkatraman et al. | |
| 2016/0150978 A1 | 6/2016 | Yuen et al. | |
| 2016/0155309 A1 | 6/2016 | Watson et al. | |
| 2016/0278712 A1 * | 9/2016 | Sagara | A61B 5/7225 |
| 2016/0374567 A1 | 12/2016 | Breslow et al. | |
| 2017/0014037 A1 | 1/2017 | Coppola et al. | |
| 2017/0020398 A1 | 1/2017 | Emadzadeh | |
| 2017/0027523 A1 | 2/2017 | Venkatraman et al. | |
| 2017/0105682 A1 | 4/2017 | MacDonald et al. | |
| 2017/0215747 A1 * | 8/2017 | van Dinther | A61B 5/0295 |
| 2018/0125381 A1 * | 5/2018 | Nakata | A61B 5/02438 |

FOREIGN PATENT DOCUMENTS

| | | |
|---|---|---|
| JP | 2002-342033 A | 11/2002 |
| WO | WO-2010/135518 A1 | 11/2010 |
| WO | 2015159187 A | 10/2015 |
| WO | WO-2016/038585 A1 | 3/2016 |
| WO | WO-2018/182911 A1 | 10/2018 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI '92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

International Search Report dated Jun. 4, 2018, for PCT Application No. PCT/US2018/020297, filed Feb. 28, 2018, five pages.

IPOS (Singapore) Search Report dated May 15, 2018, for Application No. 10201801608Q, two pages.

Danish Search Report dated Jan. 21, 2019, for Application No. PA 2018 70635, four pages.

Danish Search Report dated May 1, 2018, for DA Application No. PA 2018 70097, four pages.

\* cited by examiner

DETECTING CONDITIONS USING HEART RATE SENSORS

CROSS-REFERENCE TO RELATED APPLICATIONS

This application claims the benefit of U.S. Provisional Patent Application No. 62/478,030, filed on Mar. 28, 2017; U.S. Provisional Patent Application No. 62/480,127, filed on Mar. 31, 2017; U.S. Provisional Patent Application No. 62/541,269, filed on Aug. 4, 2017; and U.S. Provisional Patent Application No. 62/557,013, filed on Sep. 11, 2017, the entire disclosures of which are herein incorporated by reference for all purposes.

FIELD OF THE DISCLOSURE

This relates to methods for operating photoplethysmogram (PPG) sensors and the corresponding devices. More particularly, this disclosure relates to methods and devices capable of detecting irregularities in a PPG signal.

BACKGROUND OF THE DISCLOSURE

Photoplethysmogram (PPG) sensors can be used to determine physiological information of a user. In a basic form, a PPG device can employ one or more light sources and one or more light detectors. When a PPG sensor unit is positioned such that the light source(s) and the light detector(s) are placed against or in proximity to the skin of a user, the light source(s) can emit light to illuminate the user's skin. The light detector(s) can measure light incident on the light detectors to be used to determine the amount of light from the light source(s) that reaches the detector(s) (e.g., light that has transmitted, reflected, and/or scattered and exited the user's tissue). The amount of light measured by the light detectors (e.g., in the form of one or more signals) can vary based on the amount of light absorbed by the tissue of the user. The device can monitor this absorption to determine one or more physiological parameters, such as a heart rate. A relative change in the blood volume in the body's blood vessels can occur as part of the cardiac cycle (e.g., a repeated sequence of events of during which the blood vessels contract and/or relax to pump blood through the body). These relative changes may result in changes in the amount of light absorbed by the tissue of the user. These relative absorption changes may be measured by the PPG sensor and analyzed to provide measure(s) of one or more aspects of the cardiac cycle. As an example, a PPG sensor unit can measure the timing and/or characteristics of individual heartbeats. The light detector(s) can convert the measured light into an electrical signal indicative of the intensity thereof. For example, the electrical signal can be converted into a heart rate signal, which can include the information associated with timing and/or characteristics of the individual heartbeats.

In some instances, one or more aspects of a user's heartbeat (and/or a pattern of heartbeats) may differ from what would typically be expected of the user under a given set of conditions. For example, a heart rate when the user is at rest can fall between 60 and 100 beats per minute, but factors such as stress or anxiety may cause the user's heart rate to exceed their typical resting heart rate. In other instances, certain conditions, including heart arrhythmias such as atrial fibrillation, may cause irregular heart rate patterns, such as an increase in the variance in beat-to-beat timing over time. When using a sensor to monitor a user's cardiac patterns, it may be desirable for the measured signal of heartbeats to reflect irregular pulse rhythms, fast heart rates, etc., when they may occur. Some devices, however, may not be able to detect the irregularity in a signal, and other devices may not be able to distinguish between irregularity due to the user's physiological condition and noise (e.g., motion artifacts).

SUMMARY OF THE DISCLOSURE

This disclosure relates to methods for measuring irregularities in a signal (e.g., a heart rate signal) and the corresponding devices. The devices can include a PPG sensor unit configured to use a sampling procedure to detect multiple occurrences of a given event in the measured signal(s) over a sampling interval. An event may be an instance of the signal(s) satisfying one or more criteria. In some instances, the device can register (e.g., store, notify the user, etc.) the occurrences of the events. In some examples, the device can include one or more motion sensors configured to detect whether the device is in a low-motion state. The device may delay initiating subsequent measurements when the device is not in a low-motion state to enhance measurement accuracy. Examples of the disclosure further include resetting the sample procedure based on one or more factors, such as the number of non-qualifying measurements. In some examples, the device can be configured to perform multiple measurement types (e.g., primary and secondary measurements) as part of a sampling procedure, where the primary measurements can include readings using a first set of operating conditions of the PPG sensor unit, and the secondary measurements can use a different second set of operating conditions of the PPG sensor unit.

DETAILED DESCRIPTION

Figure 1:
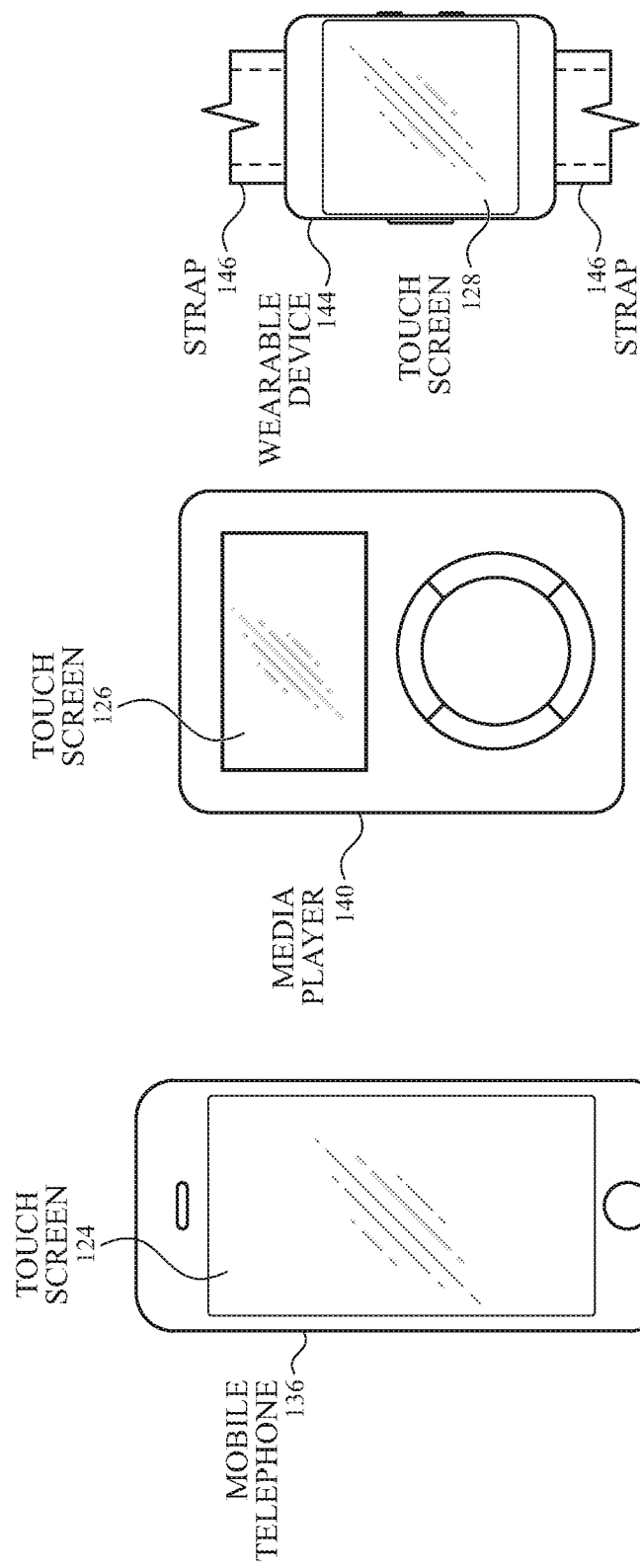
FIGS. 1A-1C illustrate devices in which examples of the disclosure can be implemented.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

This disclosure relates to devices and methods for identifying instances of events during which one or more predetermined characteristics or patterns occur in a physiological signal. Specifically, it may be desirable to identify instances of certain irregularities in a physiological signal. For example, when a physiological signal, such as a PPG signal or an electrocardiograhy (ECG) signal, measures one or more aspects of a cardiac cycle over time, it may be desirable to look for one or more predetermined characteristics of a waveform of a heartbeat and/or a pattern of heartbeats, which may be representative of corresponding characteristics present in the cardiac cycle. A physiological signal (e.g., heart rate signal) can be indicative of one or more physiological parameters (e.g., heart rate, heart rate variability, etc.) of a user. In practice, however, sensors configured to monitor these physiological signals may be susceptible to motion or other noise sources depending on the device and the mode of operation, which may reduce the accuracy with which the measured signal represents a user's actual cardiac cycle. There may be ways of improving the quality of a measured signal (e.g., by increasing the output intensity of a light source of a PPG sensor), but often times these changes may come at an increased power cost. In battery-powered devices, increasing the power used to obtain a physiological signal may reduce power available to the device for other purposes.

The examples described here mainly discuss the use of a PPG signal measured by a PPG sensor to look for one or more aspects of a heart rate signal, but it should be appreciated that the methods discussed here may be used to look for one or more predetermined characteristics in any suitable physiological signal, such as, for example an ECG signal, impedance cardiography (ICG) signal, a ballistocardiography (BCG) signal, an electromyography (EMG) signal, or the like. In these instances, the device may include one or more sensor units configured to detect some or all of the above physiological systems.

As discussed above, a PPG sensor can be used to determine one or more physiological information of a user. In a basic form, a PPG sensor unit can employ one or more light sources and one or more light detectors. When a PPG sensor unit is positioned such that the light source(s) and the light detector(s) are placed against or in proximity to the user's skin, the light source(s) can emit light to illuminate the user's skin. The light detector(s) can receive and measure light incident on the light detectors and be used to determine the amount of light from the light source(s) that reaches the detector(s) (e.g., light that has transmitted, reflected, and/or scattered and exited the user's tissue). The amount of light measured by the light detectors (e.g., in the form of one or more signals) can vary based on the amount of light absorbed by the user's tissue. The device can monitor this absorption to calculate one or more physiological information, such as a heart rate. A relative change in the blood volume in the body's blood vessels can occur as part of the cardiac cycle, and these relative changes may result in changes in the amount of light absorbed by the tissue of the user. These relative changes may be measured by the PPG sensor to look at one or more aspects of the cardiac cycle. As an example, a PPG sensor unit can measure the timing and/or characteristics of individual heartbeats to provide a measure, such as heart rate. The light detector(s) can convert the measured light into an electrical signal indicative of the intensity, and the electrical signal can be converted into a PPG heart rate signal.

When a sensor such as a PPG sensor measures a cardiac signal, the systems and methods described here may identify and register instances where one or more aspects of the measured signal meets one or more predetermined criteria. For example, the signal may be analyzed to determine a heart rate, and the systems and methods may be configured to identify instances where a heart rate exceeds a heart rate threshold value. In other instances, the signal may be analyzed to look at one or more parameters relating to the beat-to-beat timing of a series of heartbeats. For example, the systems and methods described here may identify instances where a measure of the variance of inter-beat intervals satisfies one or more variance criteria. Identifying instances of irregular inter-beat intervals may be reflective of one or more conditions underlying user conditions.

This disclosure relates to methods for measuring irregularities or other predetermined characteristics in one or more signals (e.g., a physiological signal such as a heart rate signal) and the corresponding devices. The device can include a PPG sensor unit configured to utilize a sampling procedure to detect multiple occurrences of a given event in the measured signal(s) over a sampling interval. An event may be an instance of the signal(s) satisfying one or more criteria. In some instances, the device can register (e.g., store, notify the user, etc.) an instance comprising multiple occurrences of an event (along with information about individual occurrences of the event) when the number of occurrences satisfies an occurrence threshold. In some examples, the device can include one or more additional sensors (e.g., motion sensors such as an accelerometer and/or a gyroscope), which may be used to provide additional signals. The signals may be utilized in the sampling procedure to aid in controlling the timing and/or analysis of collected signals. As an example, one or more motion sensors may be used to detect when the device is in a low-motion state (i.e., a state when the measured motion information does not meet one or more motion thresholds), and the device may delay initiating measurements when the device is not in a low-motion state to enhance measurement accuracy. In some variations, in addition to analyzing signal(s) from the PPG sensor, one or more additional signals (e.g., from a motion sensor) must also be analyzed at meet one or more corresponding criteria for the device to determine that an occurrence of an event has been measured. Examples of the disclosure further include resetting the sample procedure based on one or more factors such as the number of non-qualifying measurements.

Representative applications of methods and apparatus according to the present disclosure are described in this section. These examples are being provided solely to add context and aid in the understanding of the described examples. It will thus be apparent to one skilled in the art that the described examples may be practiced without some or all of the specific details. In other instances, well-known process steps have been described in detail in order to avoid unnecessarily obscuring the described examples. Other applications are possible, such that the following examples should not be taken as limiting.

FIGS. 1A-1C illustrate devices in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The devices of FIGS. 1A-1C can utilize the devices and methods for operating the PPG sensor unit as disclosed.

Figure 2:
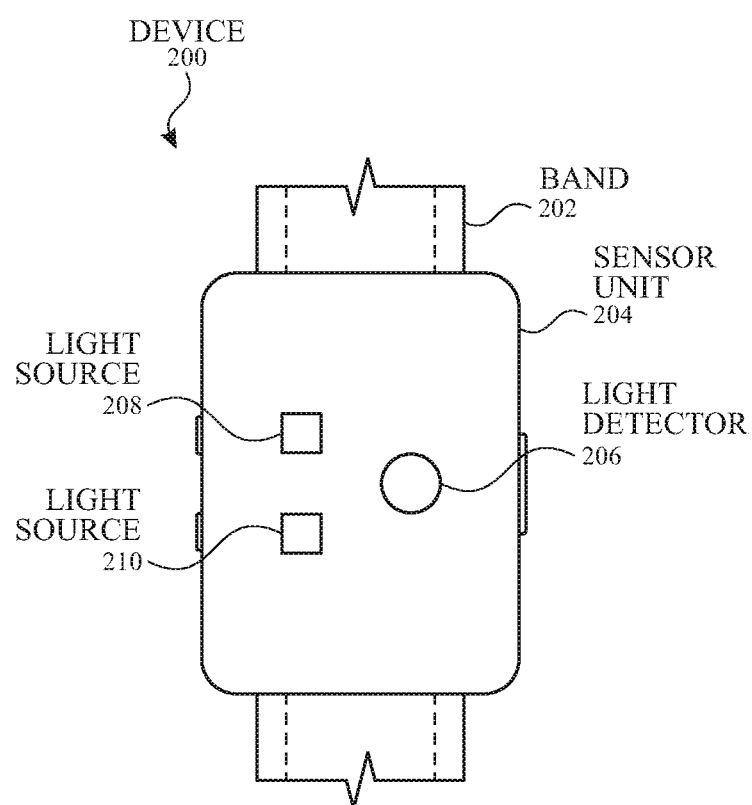
FIG. 2 illustrates a bottom view of an exemplary electronic device that includes a light detector and light sources for determining a physiological signal according to examples of the disclosure.

FIG. 2 illustrates a bottom view of an exemplary electronic device including a light detector and light sources for determining a physiological signal according to examples of the disclosure. Device 200 can include a sensor unit 204 and a band 202, which may be used to couple (e.g., attach) the sensor unit 204 to a portion of a user (e.g., a user's wrist, hand, arm, leg, or the like). The sensor unit 204 can include one or more light sources (e.g., light source 208 and light source 210) and one or more detectors (e.g., light detector 206) located on a surface of device 200. Device 200 and/or sensor unit 204 can be situated such that light sources 208 and 210 and light detector 206 are proximate to the user's skin. For example, device 200 can be held in a user's hand or strapped to a user's wrist, among other possibilities.

Light source 208 and light source 210 can emit light. The emitted light can be incident on the user's skin and can reflect back to be detected by light detector 206. A portion of the emitted light can be absorbed by the user's skin, vasculature, and/or blood, and a portion of the emitted light can be returned back to light detector 206. The sensor unit 204 may act as a PPG sensor, and the light measured by the light detector 206 over time may be used to create a PPG signal. The PPG signal may be monitored and analyzed to identify incidences of certain signal characteristics as discussed above. In some examples, the light sources can be configured to emit different wavelengths (or wavelength ranges) of light. For example, light source 208 can be configured to emit light at a green wavelength, and light source 210 can be configured to emit at an infrared wavelength.

When different light sources emit light at different wavelengths, the sensor unit may comprise one or more light detector elements capable of detecting light at multiple of the different wavelengths (in which case emissions from the different light sources can be time multiplexed). Additionally or alternatively, one or more light detector elements tuned (e.g., using one or more filters) to measure light at a subset of the different wavelengths (e.g., the sensor unit may comprise at least one light detector element tuned to measure green light, but not infrared light, and at least one light detector tuned to measure infrared light, but not green light). It should be appreciated that sensor units may include any number of light sources and light detectors, and these elements may have any suitable relative positioning in the device. Additionally, while examples are described here as utilizing first and second wavelengths comprising green and infrared wavelengths respectively, it should be appreciated that the sensor unit may utilize any suitable wavelengths for the first, second, and any additional wavelengths, such as infrared, green, red, amber, and blue light, among other possibilities.

When a sensor unit 204 is configured to emit and measure light at multiple wavelengths, the sensor unit may take measurements using different wavelengths under certain circumstances. Sensing with different wavelengths may have different tradeoffs, such as a tradeoff between accuracy and power consumption. For example, some sensor units sensing with a first wavelength (e.g., an infrared wavelength) may consume less power than sensing with a second wavelength (e.g., a green wavelength), but may be more sensitive to certain noise sources such as user motion. In these instances, it may be desirable to limit the use of the second wavelength to times when increased accuracy is desired.

In one such example, the sensor unit 204 may be configured to sense using the first wavelength at regular sampling periods (or continuously) when the device is being worn by a user. In general, during a given sampling period or during continuous sensing, the sensor unit can sample a light detector at regular intervals, e.g., 5-20 Hz. In some variations, at one or more intervals, the sensor unit may take at least two samples. At least one sample can be taken while the sensor unit is emitting light, and at least one sample can be taken while the sensor unit is not emitting light (e.g., which may provide an indication of the amount of ambient light present). The sensor unit 204 may use some or all of these measurements to provide one or more measurements relating to the cardiac cycle (e.g., heart rate) and may further be used for on-body/off-body detection when used in a body-worn (e.g., a wrist-worn) device. In these instances, the operation of the device can be adjusted based on whether the device determines the device to be on-body or off-body. When the device makes an off-body determination, one or more functions of the device may be disabled for power saving, security, or other purposes. When the first wavelength is a wavelength outside of the visible spectrum, such as an infrared wavelength, this sensing may have the further advantage of not being readily perceptible to a user.

When sensing using a first wavelength (such as an infrared wavelength) is already being utilized for on-body/off-body detection, these signals can be monitored to provide one or more measurements of the cardiac cycle at a minimal additional power cost. Conversely, sensing using a second wavelength (such as a green wavelength) may be reserved for certain uses. In some instances, sensing with the second wavelength is done during a regular sampling period that occurs less frequently than a regular (or continuous) sampling period using the first wavelength. In other instances, sampling at the second frequency may occur in conjunction with one or more additional device functions. For example, the device may operate in a mode that tracks a workout (e.g., a session of physical activity or exercise), and the sensor unit 204 may sense using the second wavelength during at least a portion of the workout. By limiting the amount of sensing that occurs at the second wavelength, the device may conserve power. Similarly, when the devices use a sensor unit such as sensor unit 204 to monitor a physiological system, it may be desirable to balance the increased accuracy of certain sensing modes with the power cost that may be associated with that sensing.

Event Tracking

When tracking events in a monitored signal as discussed above, the device can be configured to detect multiple occurrences of a given characteristic in the measured signal(s) from one or more sensing units over a given period of time (e.g., sampling interval). An event may be an instance of the signal(s) satisfying one or more criteria during the sampling interval. For example, the signal may be used to determine the timing and/or characteristics of individual heartbeats. One or more characteristics of the individual heartbeats or beat-to-beat timing may be analyzed and compared to one or more criteria, and the device may register the occurrence of an event when the relevant criteria is met. As an example, the device can be configured to detect one or more irregular heartbeat patterns as described in more detail above. As such, at least one parameter of the signal compared to one or more corresponding criteria can include, but is not limited to, one or more aspects of the waveform of the user's heartbeat, the user's heart rate, the beat-to-beat timing, etc. The criteria can include, for example, a measured heart rate exceeding a certain value (i.e., a criteria threshold). The events can include a single occurrence and/or multiple occurrences satisfying the criteria.

Figure 3A:
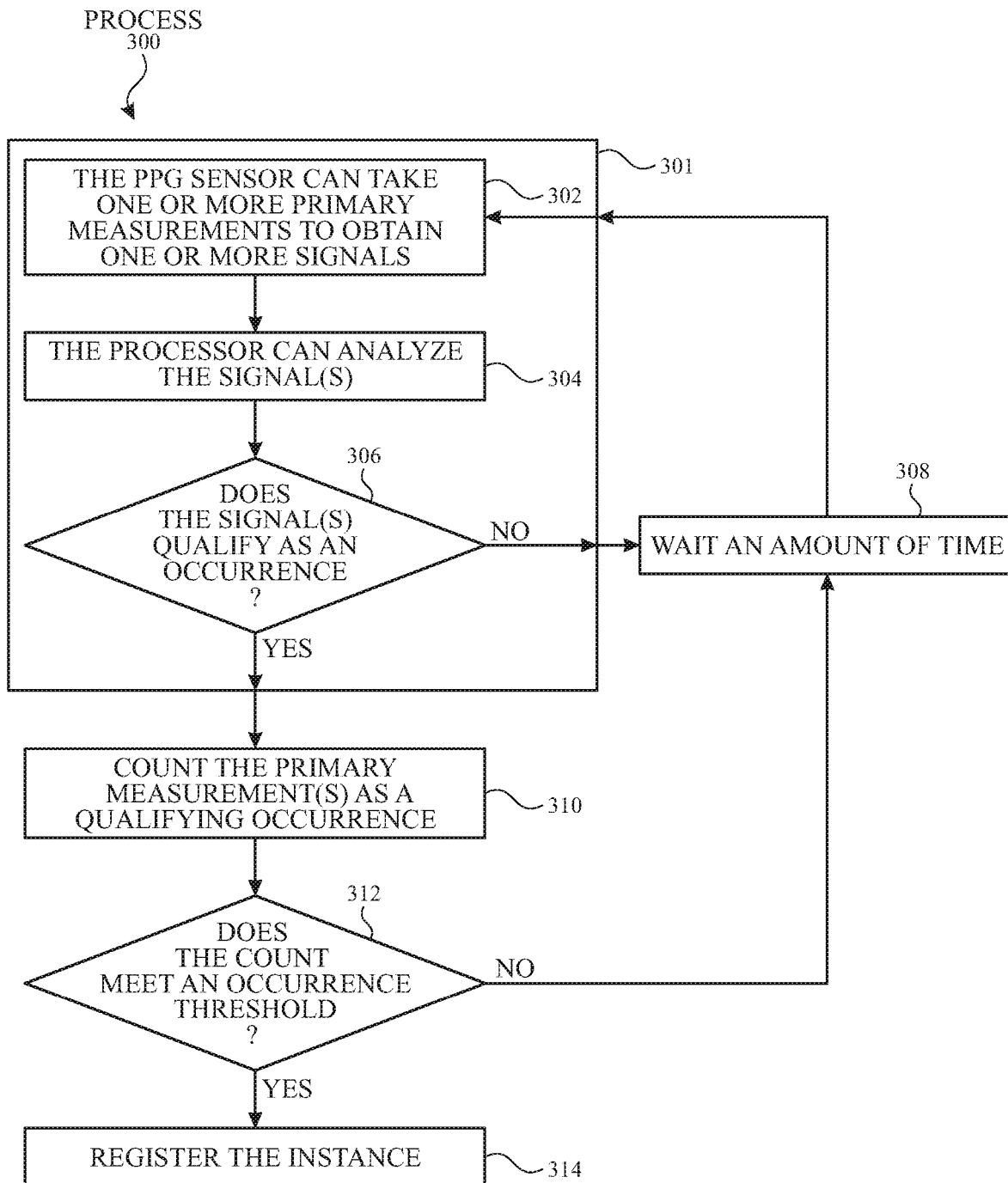
FIG. 3A illustrates an exemplary process for detecting an instance of an event using qualifying event occurrences according to examples of the disclosure.

FIG. 3A illustrates an exemplary process 300 by which a plurality of qualifying event occurrences may be used to register an instance of an event. At the start of a sampling procedure, a sensor unit, such as a PPG sensor unit, may determine whether a segment of the measured signal qualifies as an event occurrence (step 301 of process 300), as referred herein as an "occurrence determination." In some instances, making an occurrence determination comprises using the PPG sensor unit to take one or more primary measurements for obtaining one or more signals (step 302 of process 300), analyzing the signal(s) (e.g., via a processor or controller) (step 304 of process 300), and determining whether the signal(s) satisfy one or more criteria to qualify as an occurrence (e.g., step 306 of process 300). A primary measurement can be a measurement taken under a first set of operating conditions (e.g., using a given wavelength, emission intensity, sampling rate, or the like).

If the signal does not qualify as an occurrence, the device can wait an amount of time before making a new occurrence determination (e.g., at step 301) (step 308 of process 300). In these instances, at least one additional primary measurement(s) may be made (e.g., at step 302) during the subsequent occurrence determination. In some variations, the signal(s) analyzed (e.g., at step 304) may include the one or more additional primary measurements as well as one or more measurements that were analyzed in a previous occurrence determination step. In other variations, the signal(s) analyzed at step 304 may include only measurements that were taken subsequent to the previous occurrence determination. The amount of time the device waits can be predetermined or can be set based on one or more factors (e.g., the user's health condition, the user's characteristics, historical data, etc.). A signal(s) may not qualify when the signal(s) does not meet one or more criteria and/or there is insufficient information to determine whether the signal qualifies, for example. It should also be appreciated that in some instances the device may take one or more primary measurements (or secondary measurements having a different set of operating conditions) between occurrence determinations (e.g., at step 301), which may be used for other reasons (such as on-body/off-body detection or workout tracking), yet which are not used as part of an occurrence determination If the signal qualifies as an occurrence, the device can count the primary measurement(s) (measured at step 302) as a qualifying occurrence (step 310 of process 300). The processor can determine whether the number of qualifying occurrences meets (e.g., is greater than or equal to) one or more occurrence thresholds (step 312 of process 300), referred to herein as a "threshold determination." If the number of qualifying occurrences does not meet (e.g., is less than) the occurrence threshold(s), the device can wait (e.g., at step 308) before making a subsequent determination of whether a measured signal(s) qualifies as an event occurrence.

If the number of qualifying occurrences meets the occurrence threshold(s), the processor can register an instance of the event (step 314 of process 300). The occurrence threshold(s) can be a predetermined, fixed numerical value or may be based on one or more factors (discussed further below). The device can be programmed to store various occurrence thresholds and respective predetermined events. In some examples, one or more occurrence determinations of a qualifying occurrence can be weighted, such that certain qualifying occurrences may be given greater weight than other qualifying occurrences, and the occurrence threshold can be adjusted accordingly.

Figure 3B:
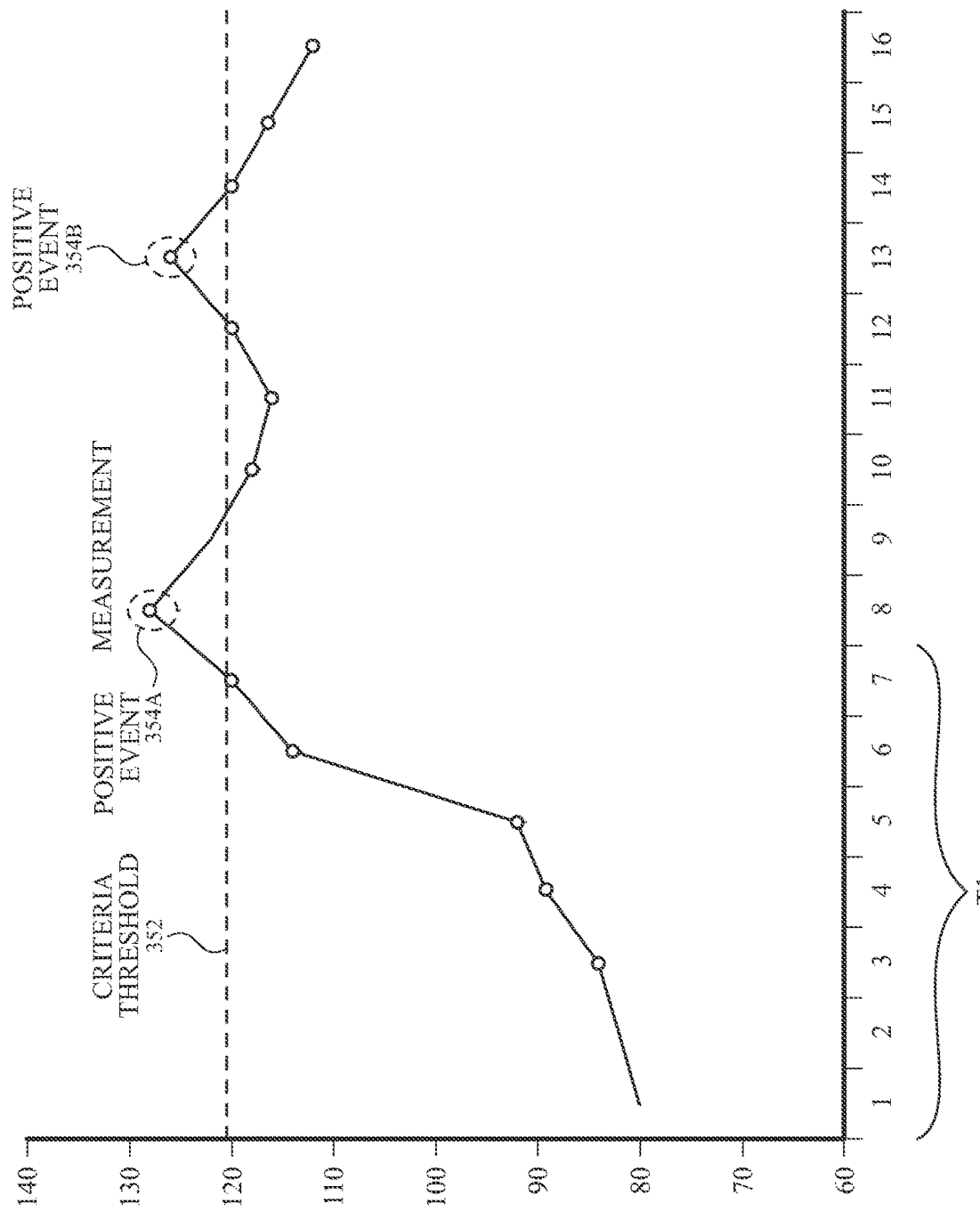
FIG. 3B illustrates an exemplary plot for detecting qualifying event occurrences according to examples of the disclosure.

As mentioned above, a qualifying occurrence may include signal segments that meet one or more criteria (e.g., one or more aspects of the waveform of the user's heartbeat, the user's heart rate, the beat-to-beat timing, etc.). FIG. 3B shows a plot that illustrates one variation of detecting a qualifying occurrence according to examples of the disclosure. In these variations, a segment of the PPG signal may be analyzed (at step 304 of process 300) to provide heart rate readings. A determination of a qualifying event (at step 306 of process 300) may occur when a heart rate reading exceeds a criteria threshold 352. The plot of FIG. 3B shows heart rate values at different determination points (illustrated with circles) relative to the criteria threshold 352. For example, the criteria threshold 352 may be 120 beats per minute (BPM), which may be a programmable threshold value.

In some of these variations, the primary measurements may be taken (e.g., at step 302 of process 300) using at least one light source emitting at infrared wavelengths to provide the PPG signal. The analysis of the PPG signal may optionally use one or more additional signals (e.g., from a motion sensor such as an accelerometer), which may in turn improve the accuracy of the determined heart rate values. Additionally or alternatively, a signal from a motion sensor must also satisfy one or more criteria for the PPG signal to be considered a qualifying event. This may be useful in instances where it is desirable to identify elevated heart rates while a user is in a rest state (e.g., where the motion sensor does not indicate activity or exercise for which the criteria threshold heart rate would normally be expected).

Each heart rate determination may be compared to the criteria threshold, and determinations exceeding the threshold (e.g., positive events 354A and 354B) may be designated as qualifying occurrences. As illustrated in FIG. 3B, up until the end of time T1, no signals qualified as the occurrence of an event. At the eighth time point, the sensing unit can detect that the user's heart rate met the criteria threshold 352 and can determine that the eighth signal qualified as a positive event 354A.

Figure 3C:
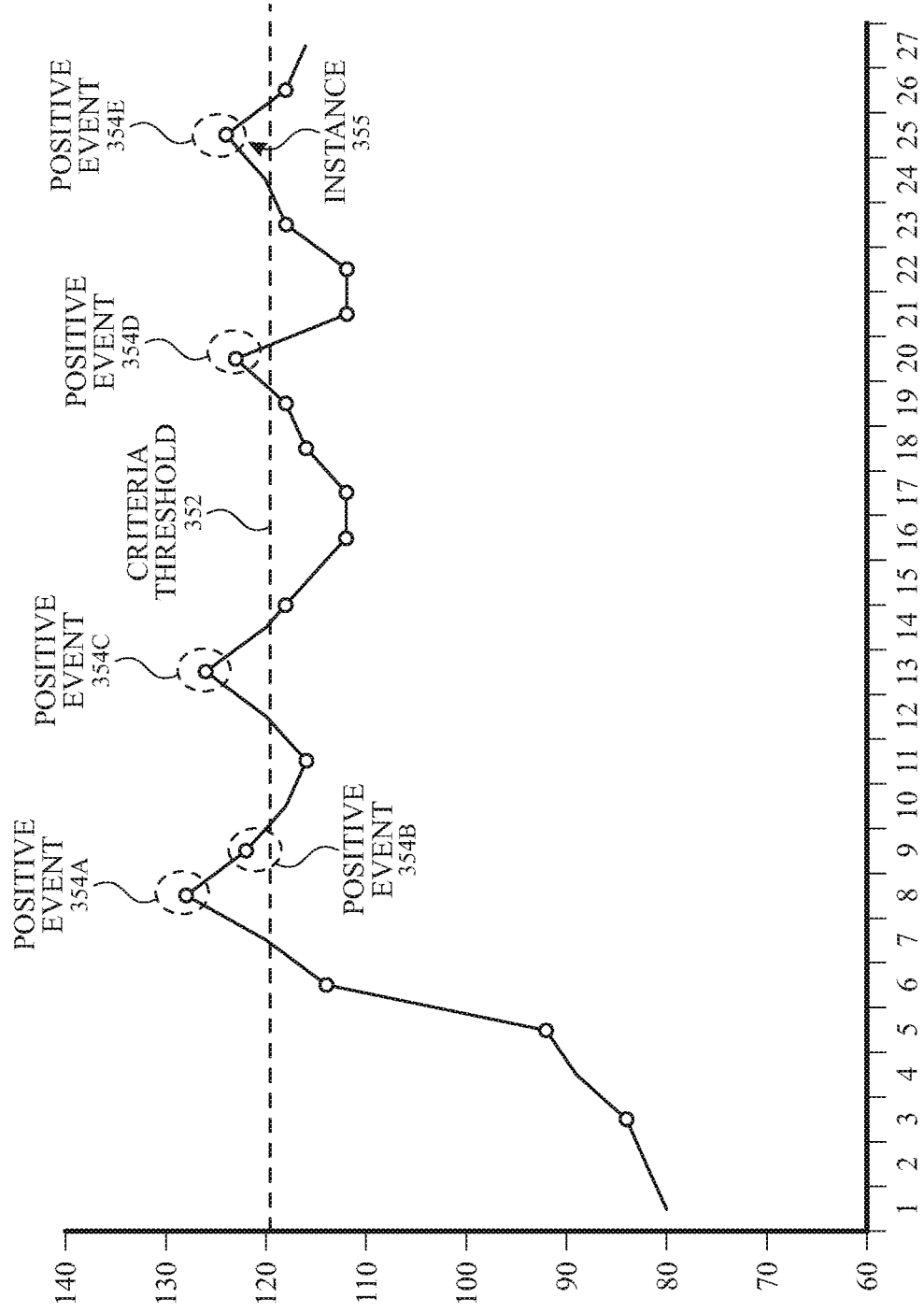
FIG. 3C illustrates an exemplary plot for registering an instance according to examples of the disclosure.

If the occurrence threshold is larger than two (for example, five occurrences), the positive events 354A and 354B may not trigger a determination of an instance of the event unless one or more additional qualifying events occur before the sampling procedure is reset. For example, the occurrence threshold may be five occurrences. Upon detecting positive events 354A and 354B, the device may determine that the count (e.g., two qualifying occurrences) may not meet the occurrence threshold during an instance determination. As illustrated in FIG. 3C, with the occurrence of positive event 354A, positive event 354B, positive event 354C, positive event 354D, and positive event 354E, the device can register instance 355.

The occurrence threshold(s) can be a predetermined, fixed numerical value or may be based on one or more factors (discussed further below). The device can be programmed to store various occurrence thresholds and respective predetermined events. In some examples, at least one primary measurement that qualifies as an occurrence can be weighted, such that certain occurrences may be given greater weight than other occurrences, and the occurrence threshold can be adjusted accordingly. As an example, in the variation discussed above with respect to FIGS. 3B and 3C, the weight of a qualifying occurrence may be doubled if a measured heart rate exceeds 150 BPM. In such an example, there may be multiple ways for an instance determination to be registered as an instance of the event (e.g., five measurements between 120 and 150 BPM or two measurements above 150 BPM and a third measurement above 120 BPM).

Figure 3D:
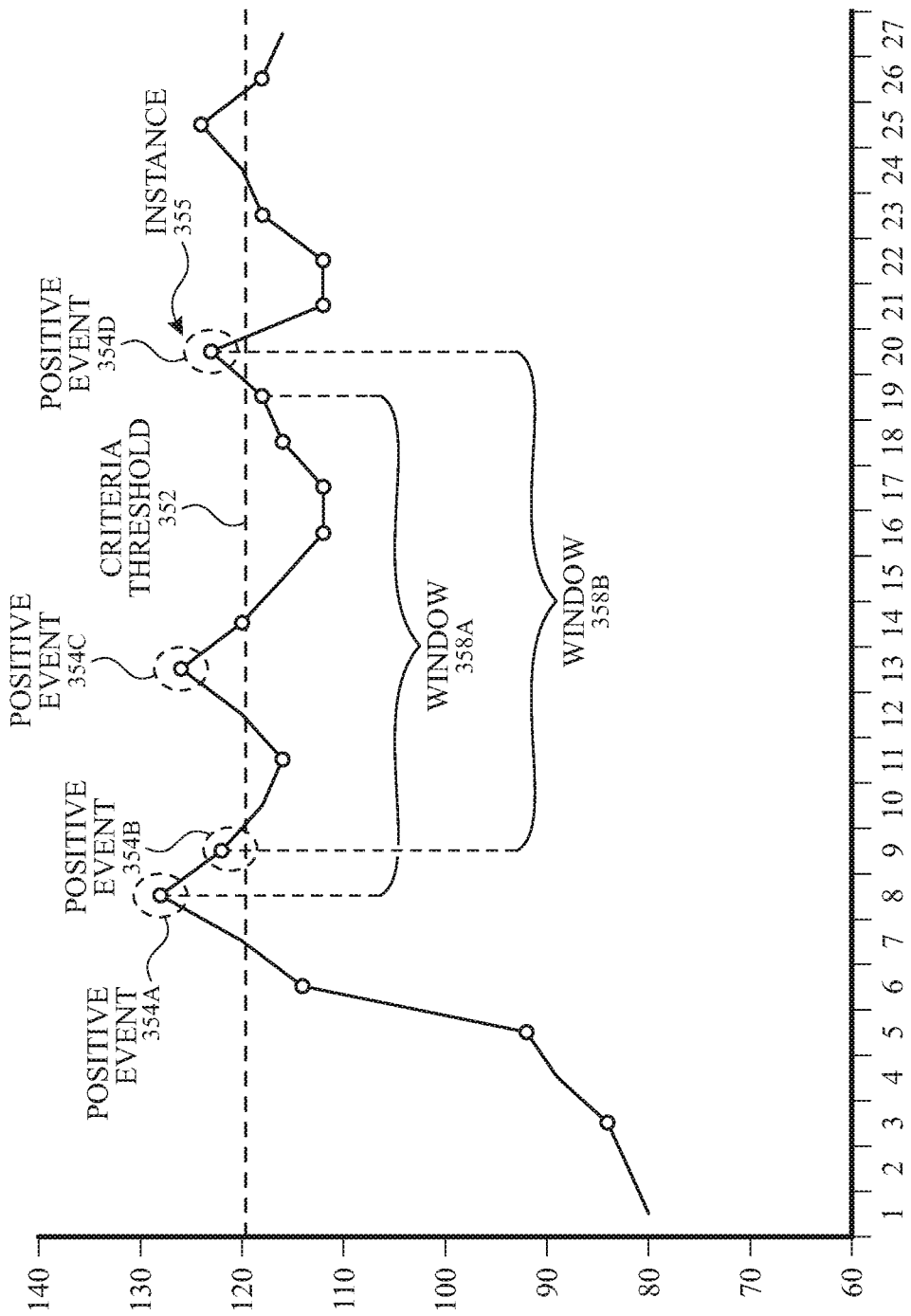
FIG. 3D illustrates an exemplary plot for detecting qualifying event occurrences within a window according to examples of the disclosure.

In some examples, an instance may be registered based on a certain number of positive events occurring within a predetermined amount of time. FIG. 3D, which shows a plot similar to those of FIGS. 3B and 3C, illustrates one such example where the occurrence threshold may be set to three events that occur within a predetermined window. Positive event 354A may trigger the beginning of window 358A. As shown in the figure, since the number of events within window 358A does not meet the occurrence threshold, an instance associated with window 358A may not be registered. Positive event 354B may trigger the beginning of a second window 358B. Since the number of positive events (e.g., positive event 354B, positive event 354C, and positive event 354D) within window 358B meets the occurrence threshold, instance 355 can be registered. The length of the window may be based on similar factors as the occurrence threshold (discussed below) and/or may be a predetermined time period. In some examples, the length of the window may be fixed, while the occurrence threshold may be adjusted (e.g., dynamically varied by the processor).

In another example of a sampling procedure, a segment of a PPG signal may be analyzed (at step 304 of process 300) to provide a measure of the regularity of the beat-to-beat timing of the PPG signal. In these variations, the one or more criteria for a qualifying occurrence may be based on a certain level of irregularity in the beat-to-beat timing. In some variations where the PPG sensor unit is capable of emitting and measuring light at both infrared and green wavelengths, it may be desirable for the primary measurements to be taken (e.g., at step 302 of process 300) using at least one light source emitting at a green wavelengths to provide the PPG signal. In some of these variations, waiting an amount of time (step 308 of process 300) between subsequent occurrence determinations may include a waiting period during which no primary measurements are taken. One or more secondary measurements (such as one or more measurements taken using an infrared wavelength) may be taken during the waiting period (e.g., for on-body/off-body detection or heart rate detection), but these measurements may not be analyzed as part of the present sampling procedure. The device, however, may use an off-body determination via one or more secondary measurements to cancel a given sampling procedure. As with the earlier examples, the device may register an instance of an event when the number of qualifying events meets (or exceeds) a corresponding occurrence threshold.

When the device registers an instance, the device may take one or more actions. In some instances, the device may create and store a flag or other record that the event has transpired. Additionally or alternatively, the device may further store information associated with the event. Examples of information that may be stored with the event include, but are not limited to, the time of the event, the associated measured signal(s), one or more metrics of the associated measured signal, information from one or more motion sensors, information about the device location (e.g., GPS data, altitude data, etc.), and usage information (e.g., whether content was being displayed on the screen). Information may be stored regarding the individual qualifying occurrences, as well as one or more measurements that may have occurred between qualifying occurrences. In some instances, the device may notify (e.g., via a haptic, visual, and/or auditory alert) the user that an instance has occurred and may further provide information to the user about event. The user may provide input (e.g., via touch input on the device's touch-sensitive display) to indicate whether the cause of the instance is known (e.g., the instance corresponds to the user jumping up and down suddenly) or unknown. If the cause of the instance is known, the device may dismiss the instance. If the cause of the instance is unknown, the device may execute one or more subsequent steps, such as notifying the user and/or transmitting information to a host device (discussed below). The host device may provide more information to the user, for example.

Occurrence Threshold

As mentioned above, in some instances the device may wait for the number of qualifying occurrences to meet (or exceed) an occurrence threshold before determining that an event has transpired. The occurrence threshold can be based on one or more factors. In some instances, the occurrence threshold may be at least partially based on one or more characteristics of the user. For example, in some variations, the occurrence threshold may be based at least in part on a user's age. In some of these instances, the occurrence threshold may decrease as a user's age increases. That is, the occurrence threshold can be a value that can be programmable by the user and/or automatically determined (and/or adjusted) based on one or more factors (e.g., the user's condition, historical measurement information, etc.). As an example, the occurrence threshold for a given user may be five when the user is younger than a certain age and can change to four when the user reaches that certain age. Other information provided by the user, such as medical condition information and medication information, could also be used in setting the occurrence threshold for a given user. The occurrence threshold may vary for different users.

The occurrence threshold may depend on the timing of the qualifying occurrences. In some instances, the device may only count qualifying occurrences that occurred within a given interval of time. As an example, the device may set an occurrence threshold for qualifying events that occurred over a span of three hours. For example, five qualifying events within a three-hour period may warrant registering (e.g., notifying the user) the event, whereas five qualifying events within a ten-hour period may be too infrequent. As another example, the device may set an occurrence threshold for qualifying events based on a certain time of the day. For example, an elevated heart rate may warrant registering the event if the elevated heart rate is detected during night hours when the user is likely sleeping.

Additionally or alternatively, the device may take into account the average time between qualifying events. For example, the device may use a first occurrence threshold when the average time between adjacent qualifying occurrences is at or below a first level and may use a different, second occurrence threshold when the average time is above the first level. In some of these instances, the device may require a fewer number of qualifying events if they occur closer together.

Motion

In some instances, the device may be configured to monitor and/or characterize device motion. For example, the device may comprise a motion sensor (e.g., an accelerometer) that may be used to measure device motion. In some instances, information about the motion may be used to help process and/or analyze the signal (e.g., in step 304 illustrated in FIG. 3A).

Figure 4A:
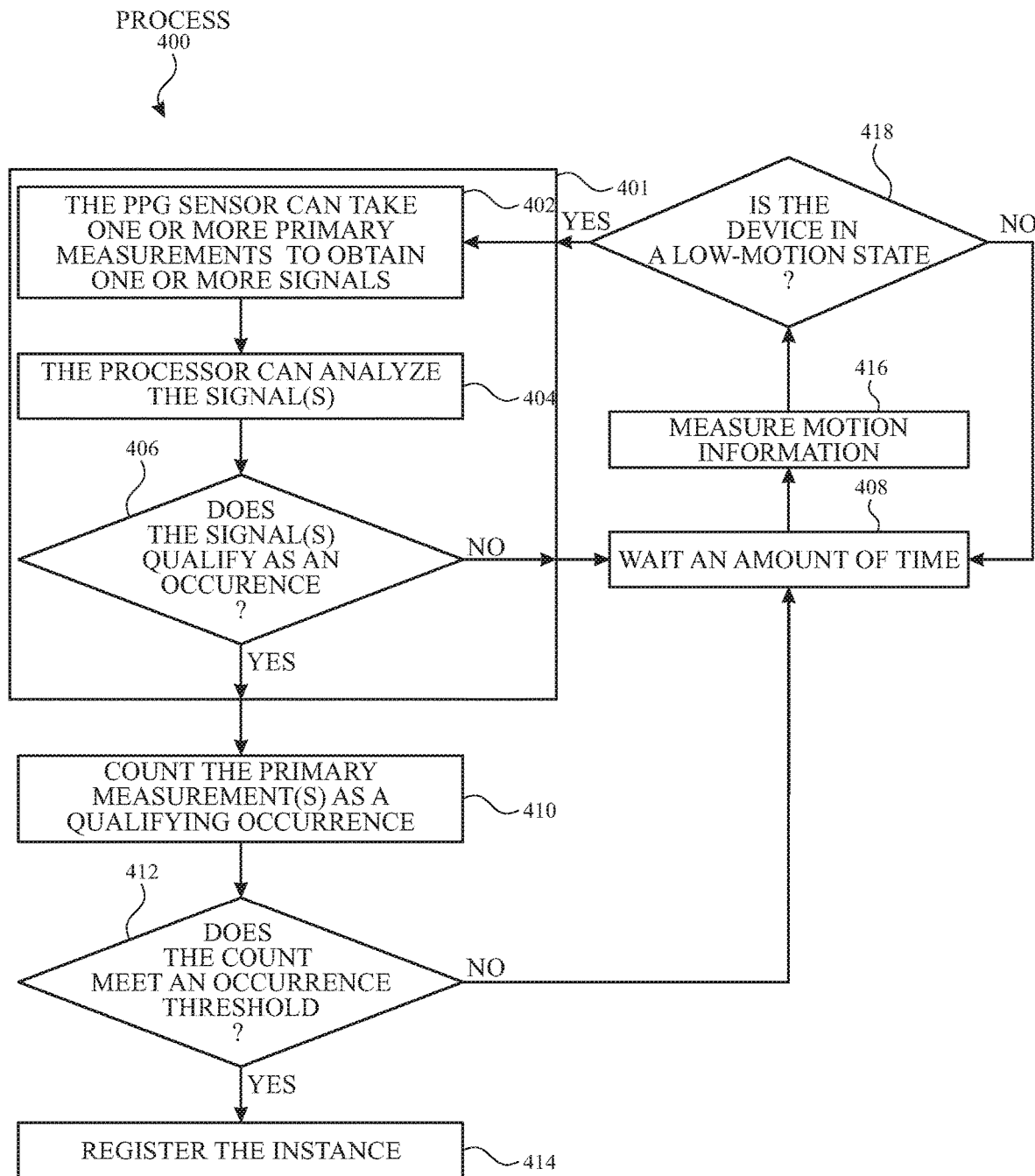
FIG. 4A illustrates an exemplary process for detecting an instance of an event using detected motion information according to examples of the disclosure.

Additionally or alternatively, the device may, in some instances, delay performing a measurement based on motion information. For example, the device may wait for the device to be in a low-motion state in order to prevent (or minimize) noise affecting the measurement. FIG. 4A illustrates an exemplary process for detecting motion information according to examples of the disclosure. The devices described here may utilize motion information to determine the timing of one or more primary measurements and/or to determine whether a signal segment qualifies as a qualifying occurrence according to examples of the disclosure. Steps 401, 402, 404, 406, 408, 410, 412, and 414 can be similar to correspondingly labeled elements from FIG. 3, except that, after waiting at step 408, the device can measure motion information (step 416 of process 400). From the motion information, the device can determine whether the device is in a low-motion state (i.e., a state when the measured motion information does not meet one or more motion thresholds) (step 418 of process 400). If the device is in a low-motion state, the device may proceed to a subsequent occurrence determination. In instances where there is a waiting period between primary measurements during step 408, the device may proceed with one or more primary measurements at step 402 when it detects a low-motion state. If the device is not in a low-motion state, the device may wait further (e.g., either until the device is in a low-motion or other criteria is met, as described below) before initiating a subsequent occurrence determination. Use of motion information may be helpful in promoting the timing of measurements when a user is being relatively still, which may assist with the reliability and accuracy of the measurements. For example, the device may not register the instance unless the user has been relatively still for 10 minutes.

Although FIG. 4 illustrates steps 416 and 418 as occurring after step 408, examples of the disclosure can include steps 416 and 418 as occurring at any time, including, but not limited to, at the same time as step 408 and/or before step 402. Examples of the disclosure can further include interrupting and/or abandoning one or more steps if a non-low-motion state is detected while the step is being executed.

In some examples, the device can characterize the motion based on a level of activity. For example, the user's motion state can be characterized as low-motion state, moderate-motion state, and high-motion state. The moderate-motion state can be the user walking, for example. When the device detects a moderate-motion state, the device can proceed with the disclosed examples, but may set one or more criteria, thresholds, wait times, or a combination thereof based on the detected motion. The high-motion state can be the user running, for example. When the device detects the high-motion state, the device can wait until the user returns to a moderate-motion state or a low-motion state before proceeding with the detection mechanisms.

Figure 4B:
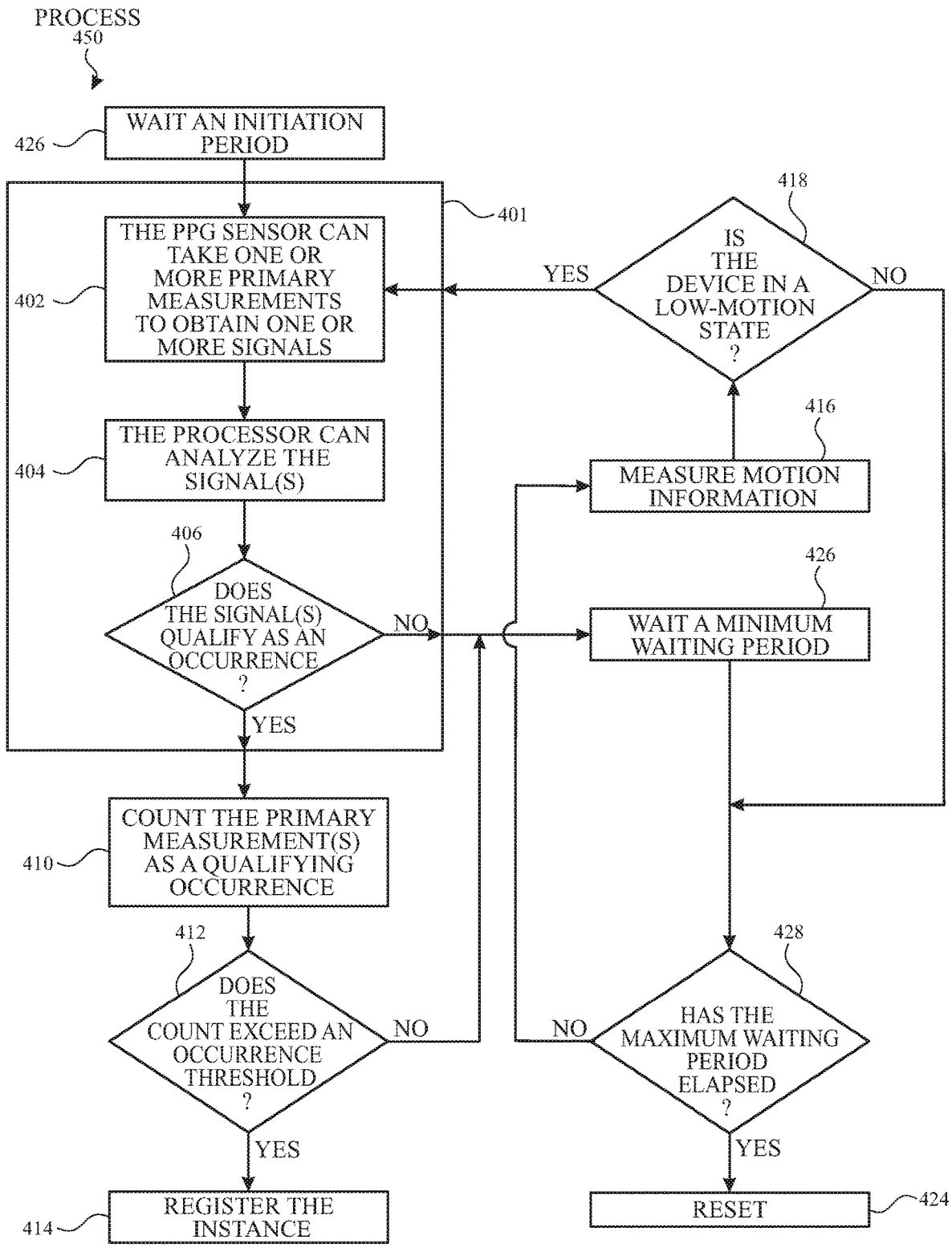
FIG. 4B illustrates an exemplary process for detecting an instance of an event that involves resetting the sampling procedure when a low-motion state has not been reached within a maximum waiting period according to examples of the disclosure.

In some examples, the sampling procedure can reset when a low-motion state has not been reached within a maximum waiting period, as illustrated in the exemplary process of FIG. 4B. The device can wait a minimum waiting period (step 426 of process 450). The device can determine whether the duration since the last occurrence determination (from step 401 of process 450) or last primary measurement 402 associated with that occurrence determination is less than the maximum waiting period (step 428 of process 450). If the time since the last occurrence determination or last primary measurement 402 associated with that occurrence determination is less than the maximum waiting period, the device can measure and determine if the device is in a low-motion state (steps 416 and 418 of process 450). If the device does not reach the low-motion state by the time the maximum waiting period has been reached, the sampling procedure can reset (step 424 of process 450).

When the sampling procedure resets at step 424, the device may reset the number of qualifying and/or non-qualifying occurrences. In some instances, the device may wait at least a reset period before attempting an occurrence determination (or a subsequent primary measurement thereof). In some instances, the duration of the reset period may depend on one or more conditions such as battery level and time of day (e.g., a larger reset period may be used if the battery level is below a certain amount at a given time of day). Additionally or alternatively, the reset period may be adjusted to provide an average rate of occurrence determinations (such as step 401 of process 400). For example, the reset period may be adjusted to provide an average rate less than or equal to one occurrence determination per hour (which may in turn depend on factors such as battery life). If, for example, the device measures, analyzes, and makes four occurrence determinations over the course of a certain time period (e.g., an hour) before the reset is initiated, the device may wait an additional amount of time (e.g., three hours) before attempting another measurement/determination.

The device may initiate a new occurrence determination and a corresponding new round of primary measurements after the reset period has elapsed. In some instances, the device may look for one or more initiation criteria at, for example, step 426 to be met before initiating the new round of primary measurements. For example, in some instances the device may initiate a new round of primary measurements if the device enters a low-motion state (which may have the same or different criteria as the low-motion determination in steps 416 and 418). Additionally or alternatively, the device may be configured to perform secondary measurements and initiate a primary measurement when the secondary measurements meet one or more criteria (which may be selected to indicate that a primary measurement would likely capture a qualify occurrence). In some instances, the device may not initiate a new occurrence determination or primary measurement thereof until one or more initiation criteria are satisfied. In other instances, the device may wait an additional period of time and at that point initiate a new occurrence determination or primary measurement regardless of whether the initiation criteria were met.

Inter-Reading Waiting Time

As discussed above, the device may wait at least a non-zero period of time before performing a subsequent occurrence determination (e.g., at step 308 illustrated in FIG. 3A or step 408 illustrated in FIG. 4A). For example, the device can wait after a given signal segment that does not qualify as an occurrence or when the number of qualifying occurrences does not meet the occurrence threshold(s). Examples of the disclosure can include the waiting period comprising a non-zero minimum waiting period (i.e., the device may not attempt a subsequent occurrence determination during the minimum waiting period). Additionally or alternatively, other factors (e.g., device motion as discussed above) may further delay the initiation of the subsequent occurrence determination. The minimum waiting period may optionally depend on whether the previous analyzed signal segment qualified as an occurrence. For example, the device may utilize a first waiting period if the previous signal segment qualified as an occurrence during the previous occurrence determination and may use a second waiting period if the previous signal segment did not qualify as an occurrence during the previous occurrence determination. In some examples, the second waiting period can be shorter than the first waiting period. Additionally or alternatively, the waiting period may depend on how close the occurrence count may be to the occurrence threshold. For example, the device may utilize a first waiting period if the occurrence count is greater than (or equal to) 90% of the occurrence threshold and may use a second shorter waiting period if the occurrence count is less than 90% of the occurrence threshold.

In some instances, one or more conditions may cause the sampling procedure to reset (e.g., the number of qualifying occurrences is returned to zero, the occurrence threshold is returned to a default value, etc.). In these instances, the device may wait at least a reset period before re-initiating a new occurrence determination. In some examples, the sample procedure may reset when a certain (e.g., predetermined threshold) number of occurrence determinations do not identify qualifying occurrences. This may include resetting when a first threshold number of successive occurrence determinations do not identify qualifying occurrences and/or a second threshold number of occurrence determinations (which do not need to be successive during the sampling procedure). In some examples that include the first and second threshold number, the second threshold number may be larger than the first threshold number (e.g., two successive occurrence determinations that do not identify a qualifying occurrence may cause a reset and three occurrence determinations spread across a sampling procedure may cause a reset). Additionally or alternatively, in instances where one or more additional conditions (e.g., a low-motion state as discussed above) may be required for performing a subsequent occurrence determination, a maximum (i.e., greater than a predetermined threshold) waiting interval between occurrence determinations may cause a reset.

Confidence Value

In some instances, counting a qualifying event can be based on a confidence value. For example, the confidence value can be used to predict, based on gross motion history within the immediately preceding time period (e.g., 2-4 minutes) or other information, the accuracy of a given occurrence determination. As an example, in high-motion settings the heart rate determined during analysis of the PPG signal is less likely to be accurate (i.e., there may be a deviation between the calculated heart rate and the actual heart rate of the user), and in these instances an identification of a qualifying occurrence may be less likely to accurately represent a corresponding occurrence happening in the user's cardiac cycle. Thus, a confidence value may be used as a representation of the accuracy of the signal measurements as well as the accuracy of a given occurrence determination.

A higher confidence value can indicate that an occurrence determination is more likely to be accurate than an occurrence determination having a lower confidence value. In some examples, a calculated confidence value must meet a threshold level in addition to the analyzed signals satisfying respective criteria thresholds in order for a signal segment to be counted as a positive qualifying occurrence. The persistence of positive events (e.g., determined by comparing the count of qualifying events relative to the occurrence threshold) can indicate an irregularity (e.g., a fast heart rate) that may merit notifying the user and/or registering the instance. In some examples, the individual occurrence determinations may be weighted based on their respective confidence values during an instance determination. For example, weighting may occur such that fewer qualifying occurrences are registered as an instance when the confidence values are higher, and vice versa.

Types of Events

Examples of the disclosure can include categorizing occurrences based on the type of event. Typically, an occurrence determination includes finding that the analyzed signal(s) is either qualifying (i.e., the analyzed signal(s) satisfies the predetermined criteria) or non-qualifying (i.e., the signal(s) does not satisfy the predetermined criteria, or the device is unable to make a determination). Typically, a qualifying event can be a positive event occurrence. A positive event can be an instance of a signal satisfying one or more first criteria over a sampling interval. Non-qualifying events may include one or more negative events. In some instance, a negative event may be an event in which the one or more first criteria of the positive event occurrence are not met. In other instances, a negative event must also satisfy one or more second criteria over the sampling interval. In these examples, negative events make up for only a subset of non-qualifying events. A first occurrence threshold can be associated with positive events, and a second occurrence threshold can be associated with negative events.

Figure 5A:
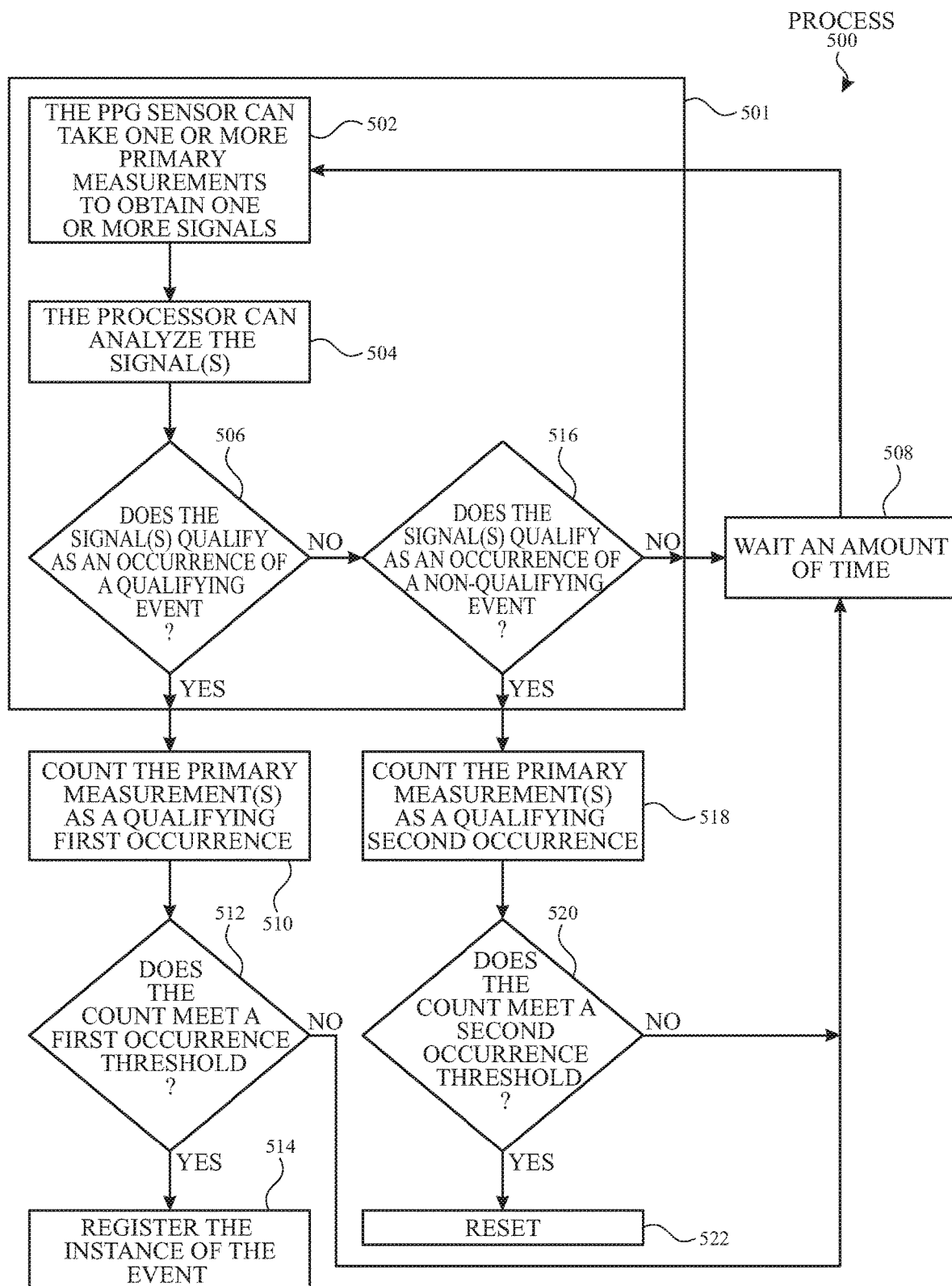
FIG. 5A illustrates an exemplary process for detecting an instance of an event using different types of event occurrences according to examples of the disclosure.

FIG. 5A illustrates an exemplary process including detecting different types of events according to examples of the disclosure. Steps 501, 502, 504, 506, 508, 510, 512, 514, and 522 are similar to correspondingly labeled elements of FIGS. 3A-4A, except as described below. The device can reset when a certain number of negative events have occurred. The device can wait an initiation period before making an occurrence determination (e.g., at step 501). During an occurrence determination at step 501, a processor may analyze the signal segment(s) to determine whether the signal segment(s) qualifies as either a first type of occurrence or a second type of occurrence. In some examples, the initiation period can differ depending on whether a sample procedure reset is due to the device powering up (e.g., from a sleep or off state) or due to one or more conditions prompting the reset (e.g., at step 522).

When a measured signal (e.g., at step 502) does not qualify as a first type of occurrence (e.g., an occurrence of a positive event as determined in steps 504 and 506), the device may determine whether the signal qualifies as an occurrence of a second type of occurrence (e.g., an occurrence of a non-qualifying event as determined in step 516 of process 500). In instances where a negative event represents a subset of non-qualifying events, a determination of the occurrence of the second type of occurrence may be limited to negative events. Accordingly, the device can count the number of qualifying positive event occurrences as a first type of occurrence and can count the number of non-qualifying (or negative qualifying events) that qualify as a second type of occurrence (e.g., negative event 556A illustrated in FIG. 5B) (step 518 of process 500).

Figure 5B:
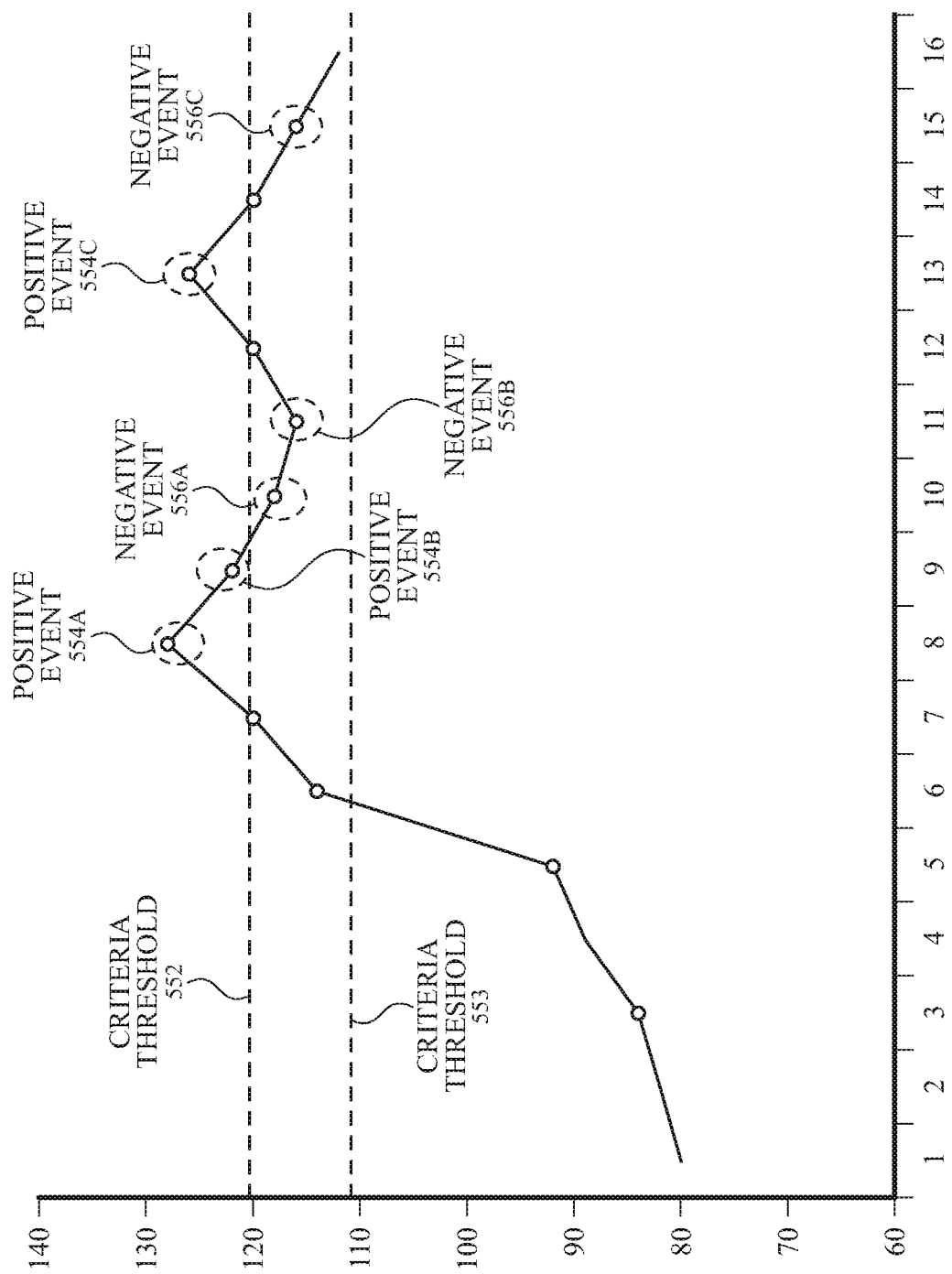
FIG. 5B illustrates an exemplary plot for detecting an instance of an event using different types of event occurrences according to examples of the disclosure.

FIG. 5B shows an example of a sampling procedure outlined in FIG. 5A. In these examples, one or more PPG signals may be analyzed to obtain a heart rate value (such as in the examples describe above with respect to FIGS. 3A-3D). In some of these examples, the first type of occurrence may occur when the measured heart rate value meets or exceeds a first criteria threshold (e.g., criteria threshold 552), and a second type of occurrence may occur when the measured heart rate value does not reach a second criteria threshold. For example, as illustrated in FIG. 5B, criteria threshold 552 may act as the first criteria threshold and the second criteria threshold, such that measurements above the criteria threshold 522 may be determined to be positive events (positive events 554A, 554B, and 554C), while measurements below criteria threshold 552 may be determined to be negative events. While the example in FIG. 5B shows that measurements equal to the criteria threshold are not considered positive or negative events (e.g., they may be considered non-qualifying events that do not contribute toward the second occurrence threshold), it should also be appreciated that, in other instances, these measurements may be considered either positive or negative events depending on the choice of boundary conditions for the criteria threshold 552.

Returning to FIG. 5A, if the number of qualifying first occurrences does not meet (e.g., is less than) the first occurrence threshold(s), the device can wait (e.g., at step 508) before making a subsequent occurrence determination (e.g., at step 501 of process 500). Similarly, if the number of qualifying second occurrences does not meet the second occurrence threshold(s), the processor can wait (e.g., at step 508) before making a subsequent occurrence determination. If the number of qualifying second occurrences meets (or exceeds) the second occurrence threshold(s) (e.g., as determined at step 520 of process 500), the processor can execute a reset procedure (described below) (step 522 of process 500). In some examples, the second occurrence threshold may be lower than the first occurrence threshold.

For example, the first occurrence threshold can be associated with positive events and may be set to five occurrences of positive events. The second occurrence threshold can be associated with negative events and may be set to three occurrences of negative events. As illustrated in FIG. 5B, measurements of the user's heart rate can lead to several qualifying occurrences in the following order: positive event 554A, positive event 554B, negative event 556A, negative event 556B, positive event 554C, and negative event 556C. At the 15$^{th}$ measurement, where negative event 556C is identified, the device may determine that the number of negative events meets the second occurrence threshold. Although three measurements qualified as positive events, the device may proceed with the reset procedure in step 522 due to the occurrence of a certain number of negative events. The occurrence of a certain number of negative events may be an indication that the detected elevated heart rates may be due to another source (e.g., noise) other than the user's heart rate or may be due to a rapidly fluctuating heart rate.

In some examples, the device may look for different types of positive or negative events include multiple criteria thresholds. For example, a first type of negative event may use a first criteria threshold 552, and a second type of negative event may use second criteria threshold 553. Occurrences of the first type of negative event may be weighted differently than occurrences of the second type of negative event, such that fewer negative events below criteria threshold 553 may lead to the reset procedure in step 522 than negative events between criteria threshold 552 and criteria threshold 553 (e.g., by weighting the negative events and/or by having multiple negative occurrence thresholds). This may be useful in distinguishing between instances where a series of measured heart rate (or other parameter) may be generally consistent, but may fall on different sides of a threshold and instances where a series of measured heart rates may fluctuate more significantly.

Multiple Measurement Types

In some examples, the device can be configured to perform both primary and secondary measurements, where the primary measurements can include readings using a first set of operating conditions of the PPG sensor unit, and the secondary measurements can use a different second set of operating conditions of the PPG sensor unit. For example, the primary measurements may be more accurate and/or less sensitive to noise than the secondary measurements, but may consume more power. In these instances, the device may be able to perform frequent secondary measurements, but may wish to restrict the number of instances (e.g., less frequent) in which the primary measurements are used to reduce the strain on the batteries. The device can determine the battery life and select between primary or secondary measurements based on the battery life. That is, the device can switch between different operating conditions of the PPG sensor unit, wherein the operating mode may be based on one or more factors such as battery life.

As an example, the secondary measurements may be taken using a light source having a different wavelength (or wavelength range) from that of the primary measurement. For example, primary measurements (e.g., using lower power infrared light sources and emitters) may be taken be more frequently in conjunction with on-body/off-body detection as discussed above. The first instance or predetermined number of instances (e.g., following a reset of the sample procedure) of a potential event can be detected utilizing primary measurements; the device can switch over or activate one or more components for measuring the heart rate using secondary measurements (e.g., using higher accuracy light sources and emitters operating in the green wavelengths, or with a different sensing unit such as those described in more detail above). In some instances, the primary measurements may be active between occurrence determinations made using the secondary measurements, and the information from the primary measurements may be used for other analysis.

Figure 6A:
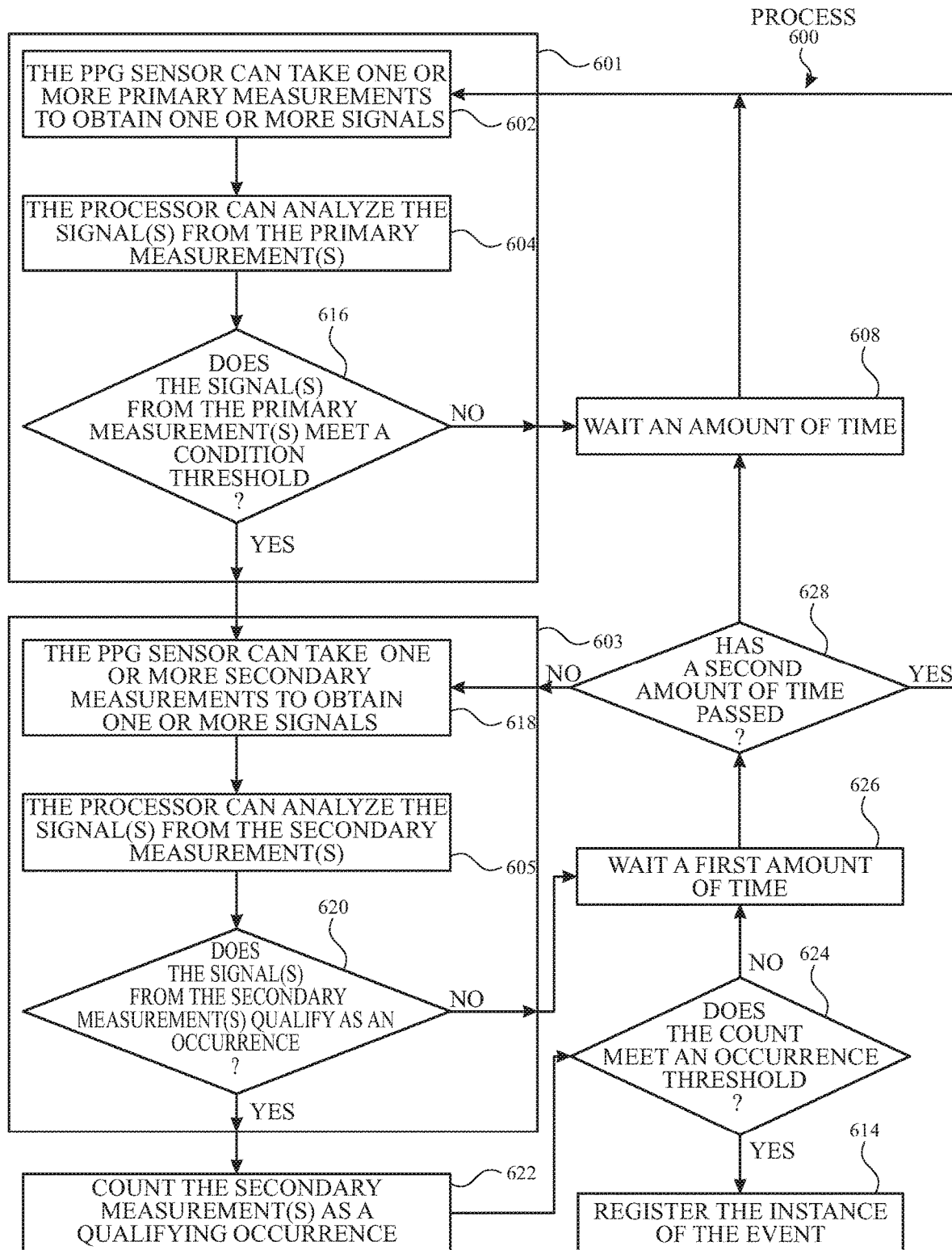
FIG. 6A illustrates an exemplary process for detecting an instance of an event using primary and secondary measurements according to examples of the disclosure.

FIG. 6A illustrates an exemplary process using primary and secondary measurements according to examples of the disclosure. Steps in FIG. 6A are similar to correspondingly labeled elements of FIGS. 3A-5, except as described below. At step 601 of process 600, a determination can be made as to whether one or more condition threshold has been satisfied for a signal segment obtained using a one or more primary measurements. Specifically, the processor can determine whether the signal(s) from the primary measurement(s) meets a condition threshold (step 616 of process 600). The condition threshold can be based on whether conditions warrant use of the secondary measurements. For example, meeting the condition threshold can be associated with an increase in confidence value associated with analysis of a signal(s) from the primary measurement. If the signal(s) from the primary measurement(s) does not meet a condition threshold, the device can wait (e.g., at step 608) before taking a subsequent primary measurement(s) (e.g., at step 601). If the signal(s) from the primary measurements(s) meets the condition threshold, the device can perform one or more occurrence determinations (e.g., at step 603). In these variations, an occurrence determination may take one or more secondary measurements to obtain one or more signals (step 618 of process 600). A processor or controller can analyze the signal(s) (step 605 of process 600) and can determine whether at least one parameter of the signal(s) from the secondary measurement(s) qualifies as an occurrence of an event (step 620 of process 600).

If the signal(s) does not qualify as an occurrence, the device can wait a first amount of time before making a subsequent occurrence determination (e.g., at step 618) (step 626 of process 600). If the signal qualifies as an occurrence, the device can count the secondary measurement(s) (e.g., measured at step 618) as a qualifying occurrence (step 622 of process 600). The processor can determine whether the number of qualifying occurrences meets (or exceeds) one or more occurrence thresholds (step 624 of process 600). If the number of qualifying occurrences does not meet (e.g., is less than) the occurrence threshold(s), the device can wait (e.g., at step 626) before taking a subsequent secondary measurement(s). If the number of qualifying occurrences meets (or exceeds) the occurrence threshold(s), the processor can register the instance (step 614 of process 600).

After waiting a first amount of time before taking a subsequent secondary measurement(s), the device can determine whether a second amount of time has passed (step 628 of process 600). If a second amount of time has passed, the device can switch to performing one or more primary measurements (e.g., at step 602). In some examples, step 628 may be based on the number of cycles or number of secondary measurements, instead of or in addition to determining whether the second amount of time has passed. In some examples, switching the device to perform one or more secondary measurements may occur at periodic intervals even if the signal(s) from the primary measurement(s) does not meet a condition threshold (e.g., determined at step 616).

As another example, the device can be configured to take secondary measurements during a non-low-motion state and can switch to taking primary measurements when a low-motion state is detected, or vice versa. Additionally or alternatively, different sampling rates (under common conditions) may be used for the primary measurements relative to the secondary measurements. In some examples, the secondary measurements can include one or more operating parameters different from the primary measurements while achieving the same operating conditions (e.g., results).

Figure 6B:
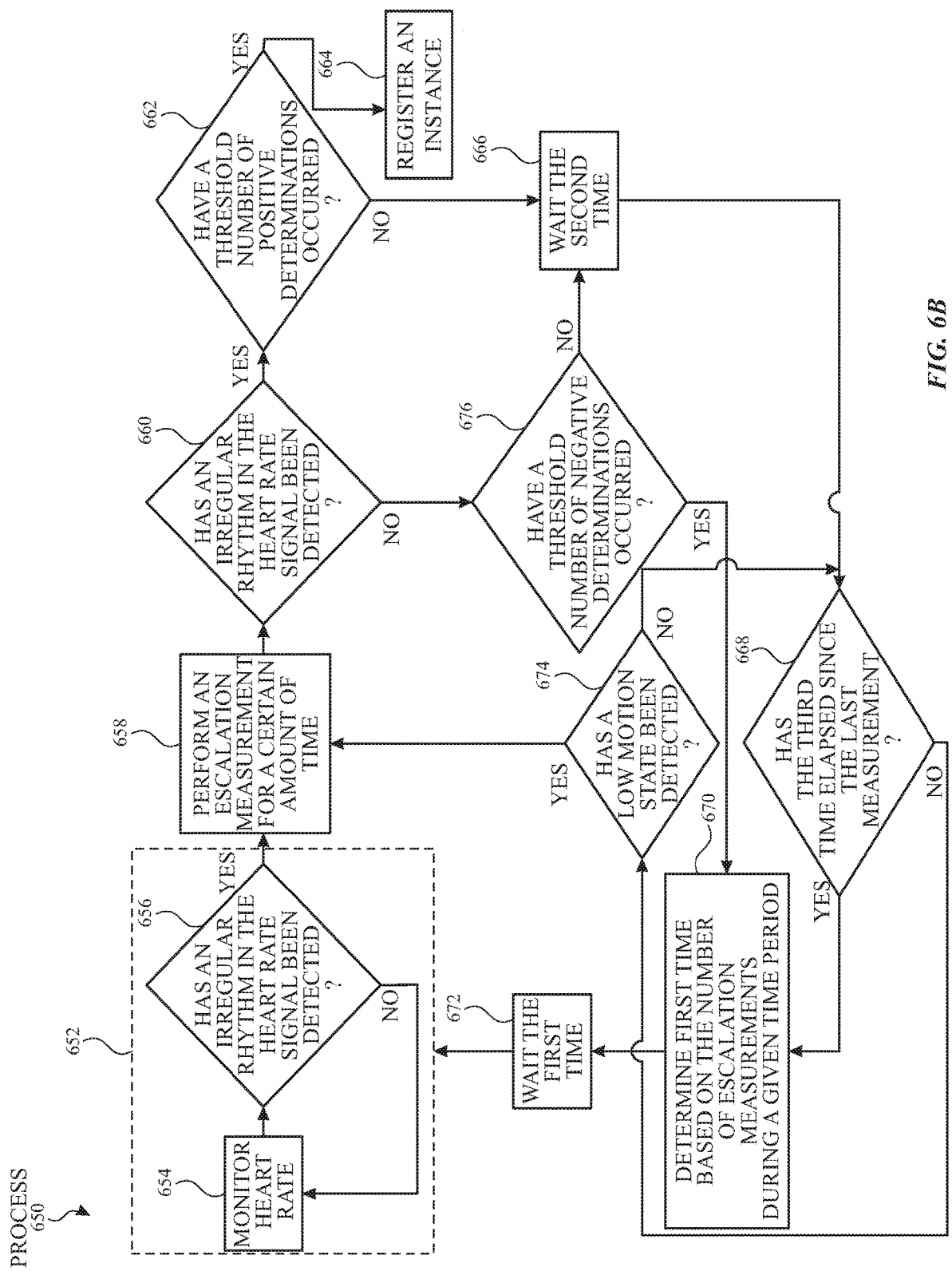
FIG. 6B illustrates an exemplary escalation procedure according to examples of the disclosure.

In some examples, the device can detect one or more irregular rhythms in the heart rate signal by using an escalation procedure. An escalation procedure can be a targeted process whereby the primary measurements are activated in response to certain criteria being met. FIG. 6B illustrates an exemplary escalation procedure according to examples of the disclosure. The process 650 can begin with monitoring the user's heart rate using the optical sensing unit (step 654 of process 650). The optical sensing unit can generate one or more heart rate signals indicative of the user's heart rate. The optical sensing unit can check the heart rate signal at predetermined intervals to determine whether the heart rate signal includes one or more irregular rhythms (process 656 of process 650). If no irregular rhythm has been detected in the heart rate signal, the optical sensing unit can continue to monitor the user's heart rate (step 654 of process 650). Examples of the disclosure include step 654 and step 656 included in step 652 as being optional steps.

If an irregular rhythm has been detected in the heart rate signal, the escalation procedure can be initiated by beginning with step 658. In some instances, the escalation procedure can be initiated based on other factors such as commands received from the processor (e.g., generated from user input).

In step 658, an escalation measurement may be performed for a certain amount of time. In some instances, the escalation measurement can include using different operating conditions from those used in step 654. In some examples, the different operating conditions can include using one or more optical components in the sensing unit for step 658 that is different from those used to monitor the heart rate in step 654. For example, the escalation measurement can include using one or more green light emitters (i.e., light emitter(s) configured to emit light in the green wavelength range) and corresponding light detector(s). The heart rate signals monitored in step 654 may include using one or more infrared light emitters (i.e., light emitter(s) configured to emit light in the infrared wavelength range) and corresponding light detector(s). In another example, the escalation measurement in step 658 can include operating the same light emitters and light detectors as in step 654 but with higher sampling frequency.

The light sensor(s) used for the escalation measurement(s) can generate one or more signals indicative of the user's heart rate during the escalation measurement time period. The system can determine whether an irregular rhythm in the heart rate signal has been detected (step 660 of process 650). If an irregular rhythm in the heart rate signal has been detected, then the device can increase (e.g., increment) the number of positive determinations. The device can determine whether a threshold number of positive determinations have been made (step 662 of process 650). A positive determination is a determination that a positive event, which indicates that an irregular rhythm has indeed been detected, has occurred. If the threshold number of positive determinations has occurred, then the device provides an indication (e.g., an indication to the user on the display, a recording of the instance to memory, a notification transmitted via wired or wireless communication to another device, etc.).

If the threshold number of positive determinations has occurred, then the device can register an instance (step 664 of process 650). If the threshold number of positive determinations has not occurred, then the device can wait a second time in step 666 before proceeding to step 668. In step 668, the device can determine whether a third time has elapsed since the last escalation measurement. If not, then the device can wait until a low-motion state has been detected (step 674 of process 650). Once a low-motion state has been detected, the device can repeat the escalation measurement (step 658 of process 650). If a low-motion state has been detected, the device can wait an additional amount of time since the last escalation measurement (step 668) before proceeding.

If the third time has elapsed since the last escalation measurement, the device can set the first time based on the number of escalation measurements during a given time period (step 670 of process 650). For example, if the last escalation measurement was performed more than an hour ago, the device may reduce the first time to avoid long time durations between measurements.

In some examples, step 668 may be based on other parameters such as the number of escalation measurements. For example, if the number of escalation measurements the device performed (e.g., four escalation measurements) during the last hour is greater than a threshold number of escalation measurements (e.g., five escalation measurements), the device may set the first time accordingly (e.g., wait an hour). In this manner, the device can conserve power consumption, for example. In another example, if the number of escalation measurements that device performed (e.g., two escalation measurements) during the last hour is less than the threshold number of escalation measurements, the device may set the first time accordingly (e.g., wait 10 minutes). In this manner, the device may increase the number of escalation measurements to improve measurement accuracy. The device can then wait the first time in step 672 before proceeding on to the optional step 652.

If, in step 660, an irregular rhythm in the heart rate signal has not been detected, the device can increase (e.g., increment) the number of negative determinations. The device can determine whether a threshold number of negative determinations has occurred (step 676 of process 650). A negative determination is a determination that a negative event, which indicates that an irregular rhythm has not been detected, has occurred. If the threshold number of negative determinations has not occurred, then the device can wait a second amount of time in step 666. If the threshold number of negative determinations has occurred, then the device can proceed to determine whether the third time has elapsed since the last escalation measurement in step 668.

Notifications

Figure 7A:
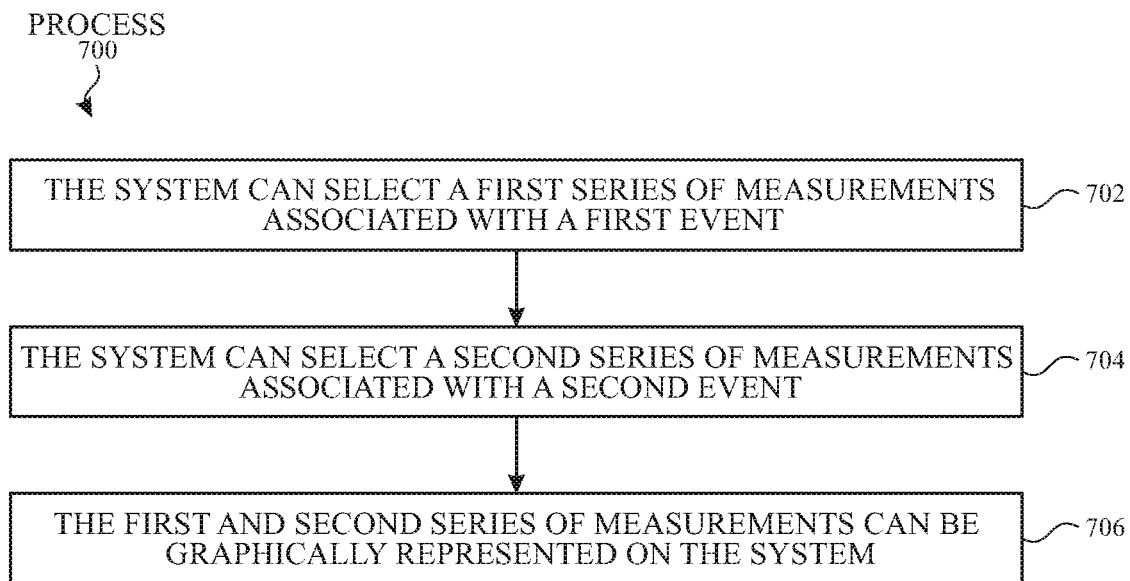
FIG. 7A illustrates an exemplary process for providing feedback to a user according to examples of the disclosure.
Figure 7B:
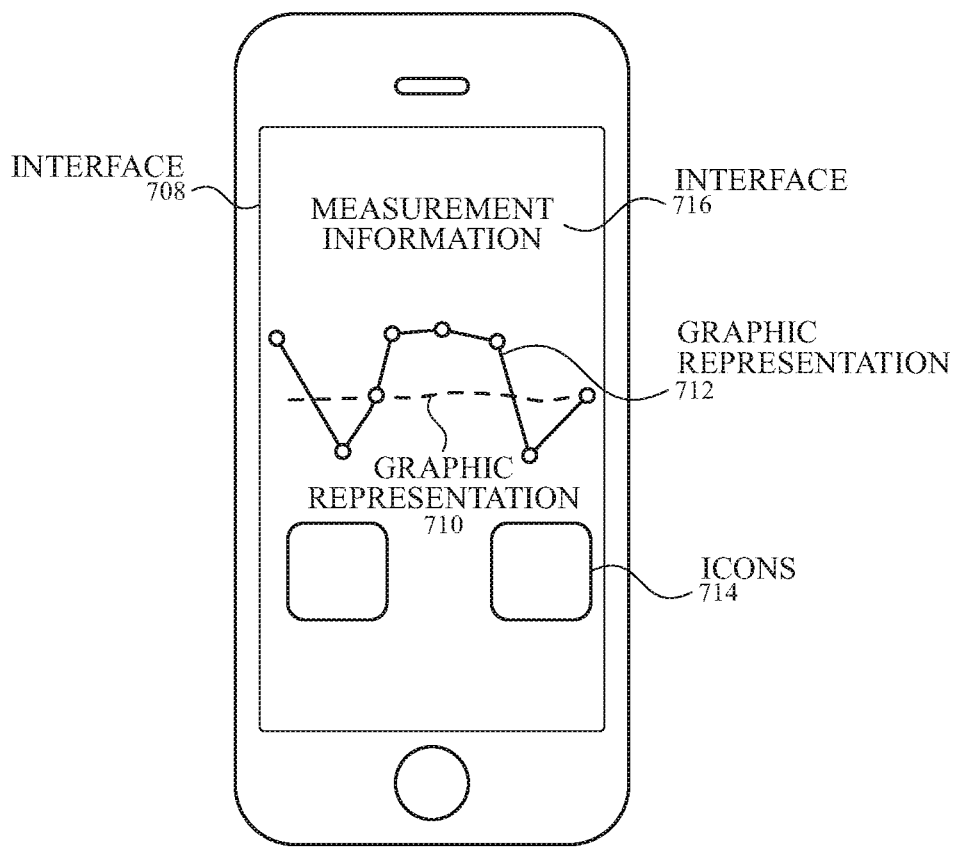
FIG. 7B illustrates an exemplary interface for providing feedback to a user according to examples of the disclosure.

As mentioned above, when the device determines that a predetermined event has transpired, the device may provide information to the user regarding that event. FIGS. 7A-7B illustrate an exemplary process 700 and a corresponding interface 708 in which the devices described here may provide feedback to a user according to examples of the disclosure. Specifically, the device may select a first series of measurements (e.g., heart rate measurements) associated with a first event (e.g., a predetermined event) (step 702 of process 700). The device may select a second series of measurements associated with a second event (step 704 of process 700). The device can graphically (e.g., via a display and a graphical user interface 716) represent the first and second series of measurement information (e.g., heart rate information) (step 706 of process 700). In some instances, the second series of heart rate measurements may be intended to illustrate an expected measurement (e.g., an average or targeted heart rate) over time. In some instances, the second series of measurements may be calculated from a plurality of series of measurements (e.g., an average of several measurements). In some instances, the second series of measurements may be selected from primary measurements that did not qualify as qualifying occurrences.

The interface 708, which may be displayed on a display (which may be part of the device including the PPG sensor unit or may be part of a separate device in communication with the device including the PPG sensor unit), may contain a graphic representation 710 of the first measurement series and a graphic representation 712 of the second measurement series. In some instances, these graphic representations may include a line chart representing a beat-to-beat timing for a measured heartbeat. In some instances, the beat-to-beat timing values (which may be represented in beats per minute) may be displayed for both series, while in other instances the values may only be displayed for the first heart rate series.

The interface may optionally include one or more icons 714, which may provide information about other instances of the predetermined event. These icons 714 may act as links to a different interface tailored specifically for those instances. Additionally or alternatively, the interface may include other graphical information (e.g., text information) 716 providing information about the predetermined event (e.g., the number of qualifying occurrences that were identified, the heart rate range of a given qualifying occurrence, etc.).

Figure 8:
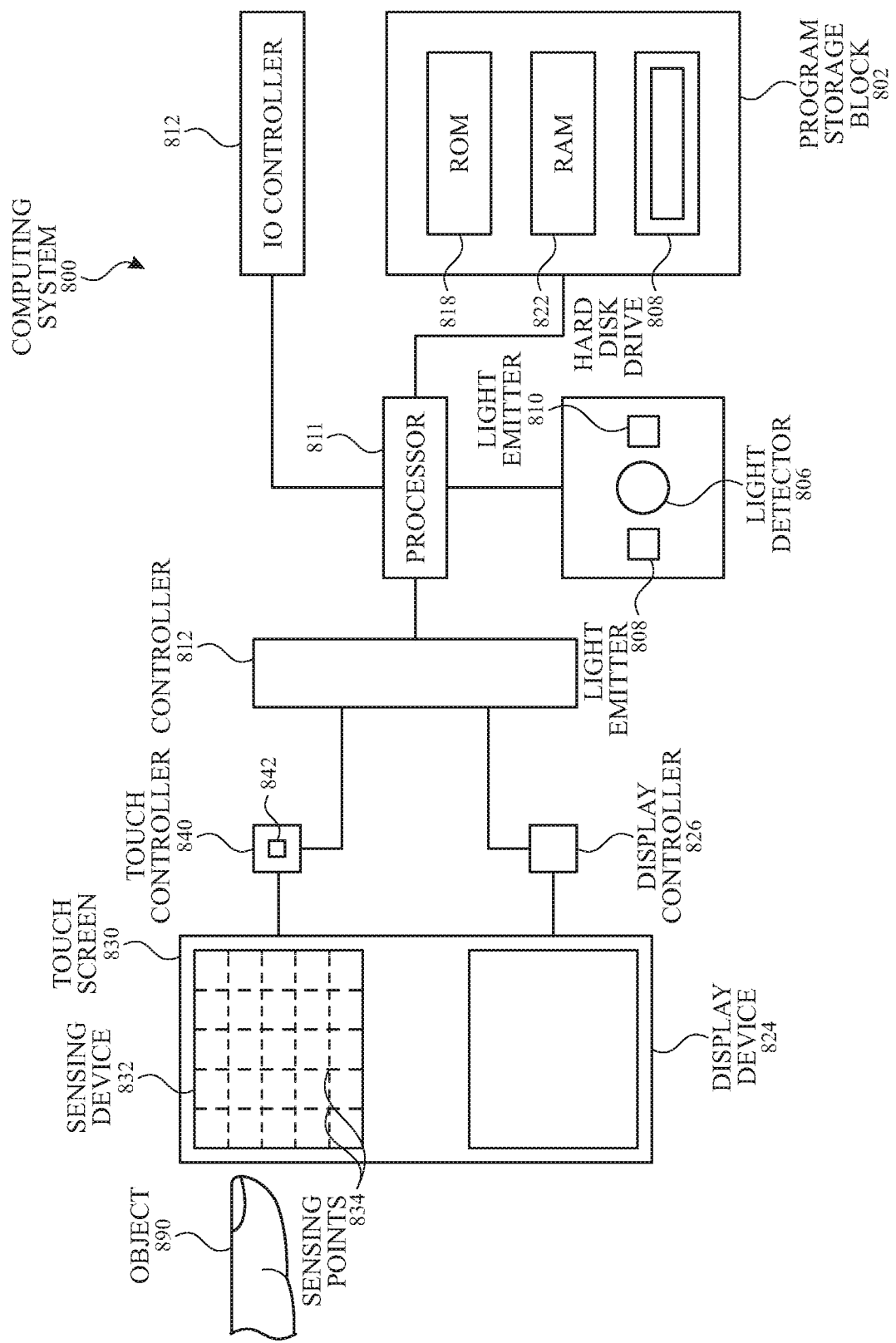
FIG. 8 illustrates an exemplary block diagram of a computing device comprising a PPG sensor unit according to examples of the disclosure.

FIG. 8 illustrates an exemplary block diagram of a computing device comprising a PPG sensor unit according to examples of the disclosure. Computing device 800 can correspond to any of the computing devices illustrated in FIGS. 1A-1C. Computing device 800 can include a processor 811 configured to execute instructions and to carry out operations associated with computing device 800. For example, using instructions retrieved from memory, processor 811 can control the reception and manipulation of input and output data between components of computing device 800. Processor 811 can be a single-chip processor or can be implemented with multiple components.

In some examples, processor 811 together with an operating device can operate to execute computer code and produce and use data. The computer code and data can reside within a program storage block 802 that can be operatively coupled to processor 811. Program storage block 802 can generally provide a place to hold data that is being used by computing device 800. Program storage block 802 can be any non-transitory computer-readable storage medium and can store, for example, history and/or pattern data relating to signal values measured by one or more light detectors, such as light detector 804. By way of example, program storage block 802 can include Read-Only Memory (ROM) 818, Random-Access Memory (RAM) 822, hard disk drive 808, and/or the like. The computer code and data could also reside on a removable storage medium and be loaded or installed onto the computing device 800 when needed. Removable storage mediums include, for example, CD-RM, DVD-ROM, Universal Serial Bus (USB), Secure Digital (SD), Compact Flash (CF), Memory Stick, Multi-Media Card (MMC), and a network component.

Computing device 800 can also include an input/output (I/O) controller 812 that can be operatively coupled to processor 811 or it may be a separate component as shown. I/O controller 812 can be configured to control interactions with one or more I/O devices. I/O controller 812 can operate by exchanging data between processor 811 and the I/O devices that desire to communicate with processor 811. The I/O devices and I/O controller 812 can communicate through a data link. The data link can be a one-way link or a two-way link. In some cases, I/O devices can be connected to I/O controller 812 through wireless connections. By way of example, a data link can correspond to PS/2, USB, Firewire, IR, RF, Bluetooth, or the like.

Computing device 800 can include a display device 824 that can be operatively coupled to processor 811. Display device 824 can be a separate component (peripheral device) or can be integrated with processor 811 and program storage block 802 to form a desktop computer (all-in-one machine), a laptop, or a handheld or tablet computing device of the like. Display device 824 can be configured to display a graphical user interface (GUI) that includes, e.g., a pointer or cursor as well as other information to the user. By way of example, display device 824 can be any type of display, including a liquid crystal display (LCD), an electroluminescent display (ELD), a field emission display (FED), a light emitting diode display (LED), an organic light emitting diode display (OLED), or the like.

Display device 824 can be coupled to display controller 826 that can be coupled to processor 811. Processor 811 can send raw data to display controller 826, and display controller 826 can send signals to display device 824. Data can include voltage levels for a plurality of pixels in display device 824 to project an image. In some examples, processor 811 can be configured to process the raw data.

Computing device 800 can also include a touch screen 830 that can be operatively coupled to processor 811. Touch screen 830 can be a combination of sensing device 832 and display device 824, where the sensing device 832 can be a transparent panel that is positioned in front of display device 824 or integrated with display device 824. In some cases, touch screen 830 can recognize touches and the position and magnitude of touches on its surface. Touch screen 830 can report the touches to processor 811, and processor 811 can interpret the touches in accordance with its programming. For example, processor 811 can perform tap and event gesture parsing and can initiate a wake of the device or powering on of one or more components in accordance with a particular touch.

Touch screen 830 can be coupled to a touch controller 840 that can acquire data from touch screen 830 and can supply the acquired data to processor 811. In some cases, touch controller 840 can be configured to send raw data to processor 811, and processor 811 processes the raw data. For example, processor 811 can receive data from touch controller 840 and can determine how to interpret the data. The data can include the coordinates of a touch as well as pressure exerted. In some examples, touch controller 840 can be configured to process raw data itself. That is, touch controller 840 can read signals from sensing points 834 located on sensing device 832 and turn them into data that the processor 811 can understand.

Touch controller 840 can include one or more microcontrollers such as microcontroller 842, which can monitor one or more sensing points 834. Microcontroller 842 can, for example, correspond to an application specific integrated circuit (ASIC), which works with firmware to monitor the signals from sensing device 832, process the monitored signals, and report this information to processor 811.

One or both display controller 826 and touch controller 840 can perform filtering and/or conversion processes. Filtering processes can be implemented to reduce a busy data stream to prevent processor 811 from being overloaded with redundant or non-essential data. The conversion processes can be implemented to adjust the raw data before sending or reporting them to processor 811.

In some examples, sensing device 832 is based on capacitance. When two electrically conductive members come close to one another without actually touching, their electric fields can interact to form a capacitance. The first electrically conductive member can be one or more of the sensing points 834, and the second electrically conductive member can be an object 890, such as a finger. As object 890 approaches the surface of touch screen 830, a capacitance can form between object 890 and one or more sensing points 834 in close proximity to object 890. By detecting changes in capacitance at the sensing points 834 and noting the position of sensing points 834, touch controller 840 can recognize multiple objects and determine the location, pressure, direction, speed, and acceleration of object 890 as it moves across the touch screen 830. For example, touch controller 890 can determine whether the sensed touch is a finger, tap, or an object covering the surface.

Sensing device 832 can be based on self-capacitance or mutual capacitance. In self-capacitance, the sensing points 834 can be provided by an individually charged electrode. As object 890 approaches the surface of the touch screen 830, the object can capacitively couple to those electrodes in close proximity to object 890, thereby stealing charge away from the electrodes. The amount of charge in the electrodes can be measured by the touch controller 840 to determine the position of one or more objects when they touch or hover over the touch screen 830. In mutual capacitance, sensing device 832 can include a two-layer grid of spatially separated lines or wires, although other configurations are possible. The upper layer can include lines in rows, while the lower layer can include lines in columns (e.g., orthogonal). Sensing points 834 can be provided at the intersections of the rows and columns. During operation, the rows can be charged, and the charge can capacitively couple from the rows to the columns. As object 890 approaches the surface of the touch screen 830, object 890 can capacitively couple to the rows in close proximity to object 890, thereby reducing the charge coupling between the rows and columns. The amount of charge in the columns can be measured by touch controller 840 to determine the position of multiple objects when they touch the touch screen 830.

Computing device 800 can also include one or more light emitters, such as light emitters 808 and 810, and one or more light detectors, such as light detector 806, proximate to the skin of the user. Light emitters 808 and 810 can be configured to generate light, and light detector 806 can be configured to measure a light reflected or absorbed by skin, vasculature, and/or blood of the user. Light detector 806 can send measured raw data to processor 811, and processor 811 can perform noise cancellation to determine the signal. Processor 811 can dynamically activate light emitters and/or light detectors based on an application, user skin type, and usage conditions. In some examples, some light emitters and/or light detectors can be activated, while other light emitters and/or light detectors can be deactivated to conserve power, for example. In some examples, processor 811 can store the raw data and/or processed information in a ROM 818 or RAM 822 for historical tracking or for future diagnostic purposes.

Figure 9:
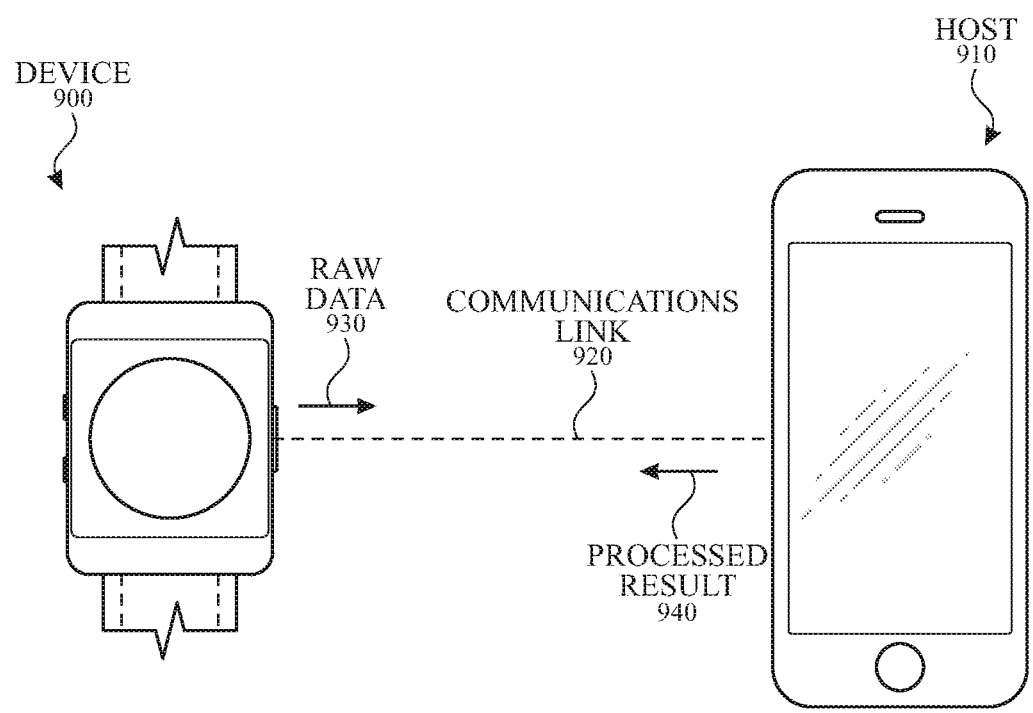
FIG. 9 illustrates an exemplary configuration in which a device is connected to a host according to examples of the disclosure.

In some examples, the light detector(s) can measure light information, and a processor can determine a signal from the reflected, scattered, and/or absorbed light. Processing of the light information can be performed on the device as well. In some examples, processing of light information need not be performed on the device itself. FIG. 9 illustrates an exemplary configuration in which a device is connected to a host according to examples of the disclosure. Host 910 can be any device external to device 900, including, but not limited to, any of the devices illustrated in FIGS. 1A-1C or a server. Device 900 can be connected to host 910 through communications link 920. Communications link 920 can be any connection, including, but not limited to, a wireless connection and a wired connection. Exemplary wireless connections include Wi-Fi, Bluetooth, Wireless Direct, and Infrared. Exemplary wired connections include Universal Serial Bus (USB), FireWire, Thunderbolt, or any connection requiring a physical cable.

In operation, instead of processing light information from the light detectors on the device 900 itself, device 900 can send raw data 930 measured from the light detectors over communications link 920 to host 910. Host 910 can receive raw data 930, and host 910 can process the light information. Processing the light information can include canceling or reducing any noise due to artifacts and determining physiological signals such as a user's heart rate. Host 910 can include algorithms or calibration procedures to account for differences in a user's characteristics affecting signal. Additionally, host 910 can include storage or memory for tracking a signal history for diagnostic purposes. Host 910 can send the processed result 940 or related information back to device 900. Based on the processed result 940, device 900 can notify the user or adjust its operation accordingly. By offloading the processing and/or storage of the light information, device 900 can conserve space and power, enabling device 900 to remain small and portable, as space that could otherwise be required for processing logic can be freed up on the device.

In some examples, registering the instance (e.g., at step 314 illustrated in FIG. 3, at step 414 illustrated in FIG. 4, or at step 514 illustrated in FIGS. 5A-5B) can include sending information related to the PPG signal(s) to the device 900 (e.g., a watch). Device 900 may display at least a portion of the information on the interface (e.g., interface 708 illustrated in FIG. 7B) and may send at least a portion of the information (e.g., as raw data 930) to host 910 (e.g., a mobile telephone) via communications link 920. The portion of the information sent to the host 910 can include the same or different information displayed by device 900.

The operations in the processes described above are, optionally, implemented by running one or more functional modules in an information processing apparatus, such as general purpose processors (e.g., as described with respect to FIG. 8) or application-specific chips. For example, processor 811 can analyze one or more signals from the sensing unit (e.g., including light emitter 808, light emitter 810, and light detector 806) (e.g., at step 304 illustrated in FIG. 3A). As another example, an instance can be registered (e.g., at step 414 illustrated in FIG. 4A) using program storage block 802.

For example, displaying operation 702, receiving operation 704, transitioning operation 708, and replacing operation 710 are, optionally, implemented by event sorter 170, event recognizer 180, and event handler 190. Event monitor 171 in event sorter 170 detects a contact on touch-sensitive surface 604, and event dispatcher module 174 delivers the event information to application 136-1. A respective event recognizer 180 of application 136-1 compares the event information to respective event definitions 186 and determines whether a first contact at a first location on the touch-sensitive surface corresponds to a predefined event or sub-event, such as selection of an object on a user interface. When a respective predefined event or sub-event is detected, event recognizer 180 activates an event handler 190 associated with the detection of the event or sub-event. Event handler 190 optionally utilizes or calls data updater 176 or object updater 177 to update the application internal state 192. In some embodiments, event handler 190 accesses a respective graphical user interface updater 178 to update what is displayed by the application. Similarly, it would be clear to a person having ordinary skill in the art how other processes can be implemented based on the components depicted in FIGS. 1A-1B.

A method is disclosed. In some examples, the method may comprise: measuring one or more physiological signals; for at least one of the one or more physiological signal measurements: determining whether at least one parameter of the one or more physiological signals meets a criteria threshold; in accordance with the determination that the at least one parameter meets the criteria threshold, increasing an occurrence value; determining whether the occurrence value meets an occurrence threshold; and, in accordance with the determination that the at least one parameter meets the occurrence threshold, registering an instance. Additionally or alternatively, in some examples, the method further comprises: for at least one of the one or more physiological signal measurements, in accordance with the determination that the at least one parameter of the one or more physiological signals meets the criteria threshold, waiting a first amount of time; and measuring one or more subsequent physiological signals. Additionally or alternatively, in some examples, the method further comprises: measuring motion information; determining whether the motion information meets a motion threshold; and, in accordance with the determination that the motion information meets the motion threshold, delaying the measurement of the one or more subsequent physiological signals. Additionally or alternatively, in some examples, the method further comprises: for at least one of the one or more physiological signal measurements: in accordance with the determination that the at least one parameter of the one or more physiological signals does not meet the criteria threshold, waiting a second amount of time, wherein the second amount of time is less than the first amount of time. Additionally or alternatively, in some examples, the method further comprises: determining whether a third amount of time has elapsed since the determination that the at least one parameter of the one or more physiological signals is less than the criteria threshold; in accordance with the third amount of time elapsing, resetting a sampling procedure; in accordance with the third amount of time not elapsing, measuring motion information; determining whether the motion information meets a motion threshold; and, in accordance with the determination that the motion information does not meet the motion threshold, delaying the measurement of the one or more subsequent physiological signals. Additionally or alternatively, in some examples, registering an instance includes providing a notification to a user. Additionally or alternatively, in some examples, a graphical user interface is located on a first device, the method further comprising: sending at least a portion of the measured one or more physiological signals to a second device, separate and distinct from the first device; and displaying the notification on the graphical user interface. Additionally or alternatively, in some examples, registering an instance includes storing information associated with the event. Additionally or alternatively, in some examples, the occurrence threshold is based on one or more characteristics of a user associated with the one or more physiological signals. Additionally or alternatively, in some examples, the occurrence threshold is based on a sampling interval. Additionally or alternatively, in some examples, the occurrence threshold is based on an average time between adjacent qualifying events, wherein at least one qualifying event is associated with the increase in occurrence value. Additionally or alternatively, in some examples, the method further comprises: for at least one of the one or more physiological signal measurements: in accordance with the determination that the at least one parameter does not meet the criteria threshold, increasing a non-occurrence value; determining whether the non-occurrence value meets a non-occurrence threshold; and, in accordance with the determination that the non-occurrence value meets the non-occurrence threshold, executing a reset procedure. Additionally or alternatively, in some examples, the one or more physiological signals are PPG signals. Additionally or alternatively, in some examples, increasing the occurrence value further is in accordance with a confidence value meeting a confidence value threshold.

A device is disclosed. In some examples, one or more PPG sensor units, including: at least one light source configured to emit light and at least one light detector configured to detect a portion of a reflection of the emitted light and configured to generate one or more physiological signals indicative of the detected portion of the reflection of the emitted light; a display configured to display a graphical user interface; and logic configured to: receive the one or more physiological signals; for at least one of the one or more physiological signal measurements; determine whether at least one parameter of the one or more physiological signals meets a criteria threshold; in accordance with the determination that the at least one parameter meets the criteria threshold, increase an occurrence value and determine whether the occurrence value meets an occurrence threshold; and, in accordance with the determination that the at least one parameter meets the occurrence threshold, display a notification on the graphical user interface. Additionally or alternatively, in some examples, the method further comprises: a motion sensor configured to measure motion information, wherein the logic is further configured to: determine whether the motion information meets a motion threshold; and for at least one of the one or more physiological signal measurements: in accordance with the determination that the at least one parameter of the one or more physiological signals meets the criteria threshold, wait a first amount of time, measure one or more subsequent physiological signals, and, in accordance with the determination that the motion information meets the motion threshold, delay the measurement of the one or more subsequent physiological signals. Additionally or alternatively, in some examples, the device is capable of switching between different operating modes of at least one of the one or more PPG sensor units. Additionally or alternatively, in some examples, at least one of the one or more PPG sensor units is configured to: operate with a first set of operating conditions while measuring background heart rate and switch to operating with a second set of operating conditions after detecting a first instance, the first instance being a first determination that the at least one parameter meets the occurrence threshold. Additionally or alternatively, in some examples, the method further comprises: a transceiver configured to transmit at least a portion of the measured one or more physiological signals to a second device, separate and distinct from the device.

A method for detecting irregularities in a heart rate signal is disclosed, the method comprising: measuring one or more heartbeats; for at least one heartbeat: determining whether an intensity, a beat-to-beat timing of the heart rate signal, or both meet a criteria threshold; in accordance with the determination that the intensity, the beat-to-beat timing, or both meet the criteria threshold, increasing an occurrence count; determining whether the occurrence count is equal to the occurrence threshold; and, in accordance with the determination that the occurrence count meets the occurrence threshold, displaying a notification on a graphical user interface. Additionally or alternatively, in some examples, the intensity meets the criteria threshold, and wherein the determination of the occurrence count is within a sampling interval, the method further comprising: determining whether the sampling interval is greater than or equal to a time threshold; and displaying the notification when the sampling interval is greater than or equal to the time threshold.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

The invention claimed is:

1. A device comprising:
one or more PPG sensor units including:
at least one light source configured to emit light; and
at least one light detector configured to detect a portion of a reflection of the emitted light and configured to generate one or more physiological signals indicative of the detected portion of the reflection of the emitted light;
a display configured to display a graphical user interface; and
circuitry that:
receives the one or more physiological signals from a primary measurement taken under a first set of operating conditions using light at a first wavelength; and
for the primary measurement:
determines whether at least one parameter of the one or more physiological signals meets a criteria threshold;
in accordance with a determination that the at least one parameter meets the criteria threshold, increases an occurrence value;
determines whether the occurrence value meets an occurrence threshold;
in accordance with a determination that the occurrence value meets the occurrence threshold, displays a notification on the graphical user interface;
in accordance with a determination that the occurrence value does not meet the occurrence threshold, waits a first amount of time before taking an additional primary measurement; and
receives one or more physiological signals from a secondary measurement taken under a second set of operating conditions using light at a second wavelength between the primary measurement and the additional primary measurement.

2. The device of claim 1, further comprising:
a motion sensor configured to measure motion information,
wherein the circuitry further:
determines whether the motion information meets a motion threshold, and
for at least one of the one or more physiological signals:
in accordance with the determination that the at least one parameter of the one or more physiological signals meets the criteria threshold, waits a second amount of time;

measures one or more subsequent physiological signals; and in accordance with the determination that the motion information meets the motion threshold, delays the measurement of the one or more subsequent physiological signals.

3. The device of claim 1, wherein the device is capable of switching between different operating modes of at least one of the one or more PPG sensor units.

4. The device of claim 3, wherein the at least one of the one or more PPG sensor units is configured to:

switch to operating with the second set of operating conditions after detecting a first instance, the first instance being a first determination that the occurrence value meets the occurrence threshold.

5. The device of claim 1, wherein: the one or more PPG sensor units include at least two PPG sensor units;, wherein at least one of the at least two PPG sensor units is configured to operate in green wavelengths; and wherein at least another of the at least two PPG sensor units is configured to operate in infrared wavelengths.

6. The device of claim 1, further comprising:

a transceiver configured to transmit at least a portion of the primary measurement or secondary measurement of the one or more physiological signals to a second device, separate and distinct from the device.

* * * * *